US008257713B2

(12) United States Patent
Poobalane et al.

(10) Patent No.: US 8,257,713 B2
(45) Date of Patent: Sep. 4, 2012

(54) VACCINE

(75) Inventors: Saravanane Poobalane, Stirling (GB);
Kim Thompson, Stirling (GB);
Alexandra Adams, Stirling (GB)

(73) Assignee: University of Stirling, Stirling (GB)

( * ) Notice: Subject to any disclaimer, the term of this patent is extended or adjusted under 35 U.S.C. 154(b) by 0 days.

(21) Appl. No.: 12/678,078

(22) PCT Filed: Sep. 11, 2008

(86) PCT No.: PCT/GB2008/003063
§ 371 (c)(1),
(2), (4) Date: Mar. 12, 2010

(87) PCT Pub. No.: WO2009/034315
PCT Pub. Date: Mar. 19, 2009

(65) Prior Publication Data
US 2012/0036589 A1    Feb. 9, 2012

(30) Foreign Application Priority Data
Sep. 14, 2007  (GB) .................................. 0717911.2

(51) Int. Cl.
*A61K 39/02* (2006.01)
(52) U.S. Cl. ............... 424/234.1; 424/185.1; 424/190.1; 424/192.1; 424/193.1; 530/350
(58) Field of Classification Search .................. None
See application file for complete search history.

(56) References Cited

U.S. PATENT DOCUMENTS
6,180,614 B1   1/2001  Davis

FOREIGN PATENT DOCUMENTS
WO   WO 03/106676 A1   12/2003

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Ford Larisa A et al: "Immunization of channel catfish with a crude, acid-extracted preparation of motile aeromonad S-layer protein" Biomedical Letters, vol. 47, No. 188, 1992, pp. 355-362.
Thomas Stephen R et al: "Tyrosine phosphorylation of the tetragonal paracrystalline array of *Aeromonas hydrophila*: Molecular cloning and high-level expression of the S-layer protein gene" Journal of Molecular Biology, vol. 245, No. 5, 1995, pp. 568-581.
Kostryzynska Metal: "Antigenic Diversity of the S-Layer Proteins From Pathogenic Strains of *Aeromonas-hydrophila* and *Aeromonas-veronii* Biotype Sobria" Journal of Bacteriology, American Society for Microbiology, US, vol. 174, No. 1, Jan. 1, 1992, pp. 40-47.
Dooley J S G et al: "Surface Protein Composition of *Aeromonas-hydrophila* Strains Virulent for Fish Identification of a Surface Array Protein" Journal of Bacteriology, American Society for Microbiology, US, vol. 170, No. 2, Feb. 1, 1988, pp. 499-506.
Murray Rge et al: "Structure of an S Layer on a Pathogenic Strain of *Aeromonas-hydrophila*" Journal of Bacteriology, American Society for Microbiology, US, vol. 174, No. 6, Jun. 1, 1988, pp. 2625-2630.
Dooley J S G et al: "Isolation and Biochemical Characterization of the S-Layer Protein From a Pathogenic Aero'Monas-Hydrophila Strain" Journal of Bacteriology, American Society for Microbiology, US, vol. 170, No. 6, Jun. 1, 1988, pp. 2631-2638.
International Search Report corresponding to PCT/GB2008/003063, 7 pages, dated Sep. 4, 2009.
PCT Written Opinion corresponding to PCT/GB2008/003063, 12 pages, dated Sep. 4, 2009.

* cited by examiner

*Primary Examiner* — Jennifer Graser
(74) *Attorney, Agent, or Firm* — Gilberto M. Villacorta; Sunit Talapatra; Foley & Lardner LLP

(57) ABSTRACT

The present invention is concerned with the development of a vaccine against *Aeromonas hydrophila* for use especially in fish. The invention provides an immunogenic S-layer protein of approximately 50 kDa of *A. hydrophila* for use in the development of a vaccine, as well as the nucleic acid encoding said protein and vaccines comprising said protein or nucleic acid encoding said protein.

17 Claims, 11 Drawing Sheets

Figure 1:
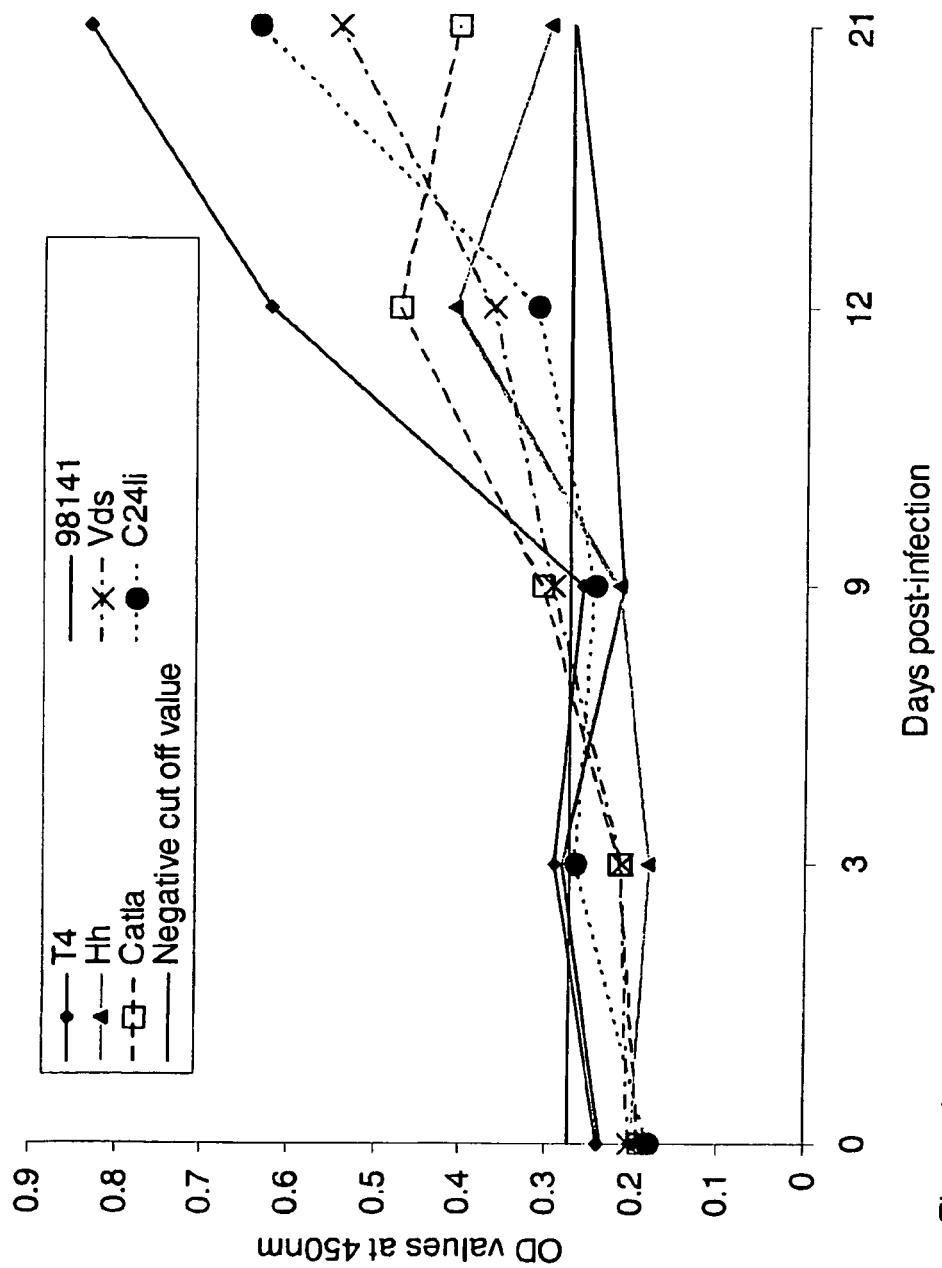

```
atgattctaatgaaaaagacactgattgcactggccgttgctggtctgagctttaacgct
 M  I  L  M  K  K  T  L  I  A  L  A  V  A  G  L  S  F  N  A
gctgcagttaatctggacactggtgctggcgtttctaagtttgctagcgaaatcaaagtt
 A  A  V  N  L  D  T  G  A  G  V  S  K  F  A  S  E  I  K  V
gatggcgcggcaggtactaccttgggtaccgcagccggtgctgctatgaatgcagtgagc
 D  G  A  A  G  T  T  L  G  T  A  A  G  A  A  M  N  A  V  S
aagctgggtttctctatttctaccggtaacaagcgttacattcgttacgatgtaactggt
 K  L  G  F  S  I  S  T  G  N  K  R  Y  I  R  Y  D  V  T  G
ggttcactggctggtgtcgctgttgcggacttgaccttggttggtggtactcctgttgct
 G  S  L  A  G  V  A  V  A  D  L  T  L  V  G  G  T  P  V  A
gtagttgcagctgatagctcctttgttatctctcagaccgccgctgatggtagctttgtg
 V  V  A  A  D  S  S  F  V  I  S  Q  T  A  A  D  G  S  F  V
atcgttgaagttgttgctaagaaagacatccctgctgatgcagtgatgacctccaaagcc
 I  V  E  V  V  A  K  K  D  I  P  A  D  A  V  M  T  S  K  A
gatggtcgtgtgaacgttaagacaaaaaatggcgtagctatcagctatcgcctgttcgag
 D  G  R  V  N  V  K  T  K  N  G  V  A  I  S  Y  R  L  F  E
actgctctggatgccgttgctaacgatccagctaagaccctggccaaggcaaatggtcaa
 T  A  L  D  A  V  A  N  D  P  A  K  T  L  A  K  A  N  G  Q
ctgctgactttctccccagctatcctcgccaaagttgagaagaagggttctgccgacaag
 L  L  T  F  S  P  A  I  L  A  K  V  E  K  K  G  S  A  D  K
atcgacgtgaccgagtcttccatgaagtttgttaccaatgcgaatgttaaagctactgat
 I  D  V  T  E  S  S  M  K  F  V  T  N  A  N  V  K  A  T  D
accatcctgggtcaagtaagcatcactgcagacgtaaacactcttttggctaacggtact
 T  I  L  G  Q  V  S  I  T  A  D  V  N  T  L  L  A  N  G  T
cccgtggctgctaccagtgatattctgaatgcaagcaaactggttgttaatggtgatttc
 P  V  A  A  T  S  D  I  L  N  A  S  K  L  V  V  N  G  D  F
tctgcaggtgcagtagacgccgataacaaactggttctgggtaccgtcaagctgaatgct
 S  A  G  A  V  D  A  D  N  K  L  V  L  G  T  V  K  L  N  A
gccaatgctactaaagttgaagccgcgaaagctgagctggctgtggcagatgcaggtatt
 A  N  A  T  K  V  E  A  A  K  A  E  L  A  V  A  D  A  G  I
ggtgcagcagctccagcaggtaacatcagctactttgttggtggcaaagctcctatcgct
 G  A  A  A  P  A  G  N  I  S  Y  F  V  G  G  K  A  P  I  A
ccgcaggctgtaactgctactttcgttccggttgtaaaagctggttatgagttggctgat
 P  Q  A  V  T  A  T  F  V  P  V  V  K  A  G  Y  E  L  A  D
gtaaatctgggcgaaattggtgtgctgaacaaaaatggttccaccaaagaagctaacctg
 V  N  L  G  E  I  G  V  L  N  K  N  G  S  T  K  E  A  N  L
gtgctggctccagataccttctacaccaacctggtgcgtatctccaacacctccaacatc
 V  L  A  P  D  T  S  Y  T  N  L  V  R  I  S  N  T  S  N  I
gctggtaagttctttgtgactgcttatgctgatgatggtaagtctgtaagcttcgcactg
 A  G  K  F  F  V  T  A  Y  A  D  D  G  K  S  V  S  F  A  L
tctgatgttgctggtcagccggctgttctggaagctggcgcctccaccaagcagatgaaa
 S  D  V  A  G  Q  P  A  V  L  E  A  G  A  S  T  K  Q  M  K
gtggctgatatctatgctgctgcccaagccaaaggtctggctctgactggtgacaagaaa
 V  A  D  I  Y  A  A  A  Q  A  K  G  L  A  L  T  G  D  K  K
ctgcgtctgaaagttgaaggtgaagtggcttccctgagcctgcagaactacaccgtctcc
 L  R  L  K  V  E  G  E  V  A  S  L  S  L  Q  N  Y  T  V  S
aaagacggtaacgctctgaacaccatgaacgcattctaa
 K  D  G  N  A  L  N  T  M  N  A  F  -
```

Figure 7

```
atgattctaatgaaaaagacactgattgcactggccgttgctggtctgagctttaacgct
 M  I  L  M  K  K  T  L  I  A  L  A  V  A  G  L  S  F  N  A
gctgcagttaatctggacactggtgctggtgtttctaagtttgctagcgaaatcaaagtt
 A  A  V  N  L  D  T  G  A  G  V  S  K  F  A  S  E  I  K  V
gatggcgcggcaggtactaccttgggtaccgcagccggtgctgctatgaatgcagtgagc
 D  G  A  A  G  T  T  L  G  T  A  A  G  A  A  M  N  A  V  S
aagctgggtttctctatttctaccggtaacaagcgttacattcgttacgatgtaactggt
 K  L  G  F  S  I  S  T  G  N  K  R  Y  I  R  Y  D  V  T  G
ggttcactggctggtgtcgctgttgcggacttgaccttggttggtggtactcctgttgct
 G  S  L  A  G  V  A  V  A  D  L  T  L  V  G  G  T  P  V  A
gtagttgcagctgatagctcctttgttatctctcagaccgccgctgatggtagctttgtg
 V  V  A  A  D  S  S  F  V  I  S  Q  T  A  A  D  G  S  F  V
atcgttgaagttgttgctaagaaagacatccctgctgatgcagtgatgacctccaaagcc
 I  V  E  V  V  A  K  K  D  I  P  A  D  A  V  M  T  S  K  A
gatggtcgtgtgaacgttaagaacaaaaatggcgtagctatcagctatcgcctgttcgag
 D  G  R  V  N  V  K  N  K  N  G  V  A  I  S  Y  R  L  F  E
actgctctggatgccgttgctaacgatccagctaagaccctggccaaggcaaatggtcaa
 T  A  L  D  A  V  A  N  D  P  A  K  T  L  A  K  A  N  G  Q
ctgctgactttctccccagctatcctcgccaaagttgagaagaagggttctgccgacaag
 L  L  T  F  S  P  A  I  L  A  K  V  E  K  K  G  S  A  D  K
atcgacgtgaccgagtcttccatgaagtttgttaccaatgcgaatgttaaagctactgat
 I  D  V  T  E  S  S  M  K  F  V  T  N  A  N  V  K  A  T  D
accatcctgggtcaagtaagcatcactgcagacgtaaacactcttttggctaacggtact
 T  I  L  G  Q  V  S  I  T  A  D  V  N  T  L  L  A  N  G  T
cccgtggctgctaccagtgatattctgaatgcaagcaaactggttgttaatggtgatttc
 P  V  A  A  T  S  D  I  L  N  A  S  K  L  V  V  N  G  D  F
tctgcaggtgcagtagacgccgataacaaactggttctgggtaccgtcaagctgaatgct
 S  A  G  A  V  D  A  D  N  K  L  V  L  G  T  V  K  L  N  A
gccaatgctactaaagttgaagccgcgaaagctgagctggctgtggcagatgcaggtatt
 A  N  A  T  K  V  E  A  A  K  A  E  L  A  V  A  D  A  G  I
ggtgcagcagctccagcaggtaacatcagctactttgttggtggcaaagctcctatcgct
 G  A  A  A  P  A  G  N  I  S  Y  F  V  G  G  K  A  P  I  A
ccgcagtctgtaactgctactttcgttccggttgtaaaagctggttatgagttggctgat
 P  Q  S  V  T  A  T  F  V  P  V  V  K  A  G  Y  E  L  A  D
gtaaatctgggcgaaattggtgtgctgaacaaaaatggttccaccaaagaagctaacctg
 V  N  L  G  E  I  G  V  L  N  K  N  G  S  T  K  E  A  N  L
gtgctggctccagataccctcttacaccaacctggtgcgtatctccaacacctccaacatc
 V  L  A  P  D  T  S  Y  T  N  L  V  R  I  S  N  T  S  N  I
gctggtaagttctttgtgactgcttatgctgatgatggtaagtctgtaagcttcgcactg
 A  G  K  F  F  V  T  A  Y  A  D  D  G  K  S  V  S  F  A  L
tctgatgttgctggtcagccggctgttctggacgctggcgcctccaccacgcagatgaaa
 S  D  V  A  G  Q  P  A  V  L  D  A  G  A  S  T  T  Q  M  K
gtggctgatatctatgctgctgcccaagccaaaggtctggctctgactggtgacaagaaa
 V  A  D  I  Y  A  A  A  Q  A  K  G  L  A  L  T  G  D  K  K
ctgcgtctgaaagttgaaggtgaagtggcttccctgagcctgcagaactacaccgtctcc
 L  R  L  K  V  E  G  E  V  A  S  L  S  L  Q  N  Y  T  V  S
aaagacggtaacgctctgaacaccatgaacgcattctaa
 K  D  G  N  A  L  N  T  M  N  A  F  -
```

Figure 8

VACCINE

CROSS-REFERENCE TO RELATED APPLICATIONS

This is a National Stage application of PCT/GB2008/003063, filed Sep. 11, 2008, which claims the benefit and priority of United Kingdom (GB) Patent Application No. 0717911.2, filed Sep. 14, 2007. The foregoing applications are incorporated by reference herein in their entirety.

FIELD OF THE INVENTION

The present invention is concerned with the development of a vaccine against *Aeromonas hydrophila* for use especially in fish. The invention provides an immunogenic S-layer protein of approximately 50 kDa of *A. hydrophila* for use in the development of a vaccine, as well as the nucleic acid encoding said protein and vaccines comprising said protein or nucleic acid encoding said protein.

BACKGROUND OF THE INVENTION

*Aeromonas hydrophila* is an important pathogen that has caused major loss in the aquaculture industry (Shotts et al., 1972; Olivier et al., 1981; Esteve et al., 1995) and attempts have been made to develop an effective vaccine (Lamers et al., 1985; Baba et al., 1988b; Leung et al., 1997; Rahman and Kawai, 2000). The effects of a number of inactivated whole cell (WC) vaccines have been reported and an increase in serum antibody levels against *A. hydrophila* was observed in common carp immersed in a preparation of heat inactivated *A. hydrophila* (Lamers et al., 1985). Kusuda et al. (1987) also found an increase in the concentration of total serum proteins, when common carp were immunised with formalin killed *A. hydrophila*. Rainbow trout immunised by injection, immersion and oral administration of killed *A. hydrophila*, have been shown to produce antibodies in their serum, bile, skin and gut mucus, and skin and muscle extracts (Loghothetis and Austin, 1994). A polyvalent vaccine containing heat killed WC and formalin inactivated extra cellular products (ECP) of *A. hydrophila* has also been tested in two Indian major carp species (rohu and mrigal), but it failed to protect the fish against bacterial challenge (Chandran et al., 2002a).

Bacteria biofilms grown on the surfaces of nutrient flakes (chitin) have been used as oral administered heat inactivated biofilm vaccines against *A. hydrophila*, and have been reported to elicit a protective response in Indian major carp (catla and rohu) and common carp (Azad et al., 1999). The biofilm vaccines have been found to be retained for longer than free cell vaccines in the tissues of gut, spleen and kidney in Indian major carp (Azad et al., 2000a). Post *A. hydrophila* challenge, Catfish, fed with biofilm vaccines showed significantly higher serum agglutinating antibody titres and relative percentage survival (RPS) values compared to those fed with free cells (Nayak et al. 2004b). When grown as a biofilm, it was noted that there was a change in *A. hydrophila* antigenicity (Asha et al., 2004). Specifically, the authors found that the S-layer proteins were lost and the Lipopolysaccharide (LPS) of the bacteria contained an additional high molecular weight band. Asha et al. (2004) suggested that this high molecular weight LPS band might elicit a protective immune response when the biofilm was administrated as an oral vaccine.

Considerable interest has been shown in bacterial OMP vaccines. Rahman and Kawai (2000) found that the OMPs of *A. hydrophila* elicited protection against an *A. hydrophila* challenge, and suggested that a vaccine based on selected OMP antigens may be effective. Munn (1994) suggested outer membrane components such as LPS could represent protective vaccine candidates for Gram-negative bacteria, while Dooley et al. (1986) reported that LPS of *A. hydrophila* posses highly immunogenic O polysaccharide chains of homogeneous length, and these were conserved both morphologically and antigenically in virulent isolates. The role of LPS in protection was also shown, in common carp vaccinated with crude LPS (Baba et al., 1988b). This protection appears to be based on cellular immunity rather than humoral immunity (Baba et al., 1988a). Similarly, Loghothetis and Austin (1996b) reported that LPS could be a major antigenic component of *A. hydrophila*.

Live WC cell vaccines have also been found to increase antibody responses in fish (Loghothetis and Austin, 1994). Other live vaccines, such as live attenuated (mutant) vaccines have also been explored for *A. hydrophila*. For example, growth-deficient mutants of *A. hydrophila* have been found to be promising live vaccine candidates in fish (Leung et al., 1997). An AroA mutant *A. hydrophila* strain was also investigated and found to be protective in rainbow trout (Moral et al., 1998). The vaccine was also found to elicit significant protection against *A. salmonicida* (Vivas et al., 2004b). Vivas et al. (2004c) suggested that this live aroA attenuated vaccine had a high level of safety compared with normal strains as it has a lower potential to survive in water. Other live vaccines have also been investigated, for example Catfish, *Clarias batrachus* immunised with plasmid free *A. hydrophila* mutants, showed an increased survival rate following challenge with wild bacteria compared to the control group (Majumdar et al., 2006). Mutant strains of *A. hydrophila* with a highly attenuated exoenzyme were also shown to confer protection in swordtail fish, *Xiphophorus helleri* (Liu and Bi, 2006).

Although all the vaccines reported have shown varying degrees of increased immunity and protection, no commercial vaccine is available for *A. hydrophila* (Loghothetis and Austin, 1996b; Rahman and Kawai, 2000; Fang et al., 2004; Vivas et al., 2005). Over 90 established or provisional serogroups within the genus *Aeromonas* have been described, and the heterologous nature of *A. hydrophila*, both biochemically and serologically are still the greatest concern for developing an effective vaccine against *A. hydrophila* (Sakazaki and Shimada 1984; Stevenson, 1988; Khashe et al., 1996; Newman, 1993; Janda et al., 1994b; Leung et al., 1995).

It is amongst the objects of the present invention to obviate and/or mitigate at least one of the aforementioned disadvantages.

It is a further object to provide a vaccine against *A. hydrophila*, which desirably exhibits broad protection to many serogroups of *A. hydrophila*.

SUMMARY OF THE INVENTION

The present invention is based on the isolation of a protein of approximately 50 kDa (as determined by SDS-PAGE) from the S-layer of *A. hydrophila* and its use to raise an immune response in an organism.

Thus, in a first aspect, the present invention provides a protein of approximately 50 kDa from the S-layer of *A. hydrophila* for use in raising an immune response in an organism. The protein may find particular application as a vaccine, but could also be used to obtain an immune serum for use in another organism.

The 50 kDa protein is encoded by a nucleotide sequence derived from *A. hydrophila* (such as a T4 isolate), and has a molecular weight of about 50 kDa. In a particularly preferred embodiment of this aspect of the invention, the 50 kDa protein is encoded by the nucleotide sequence as shown in FIG. 8 or 9, representing the coding region of the immunogenic S-layer protein of *A. hydrophila* of the present invention, and having the amino acid sequence as shown.

Figures 9, 10:
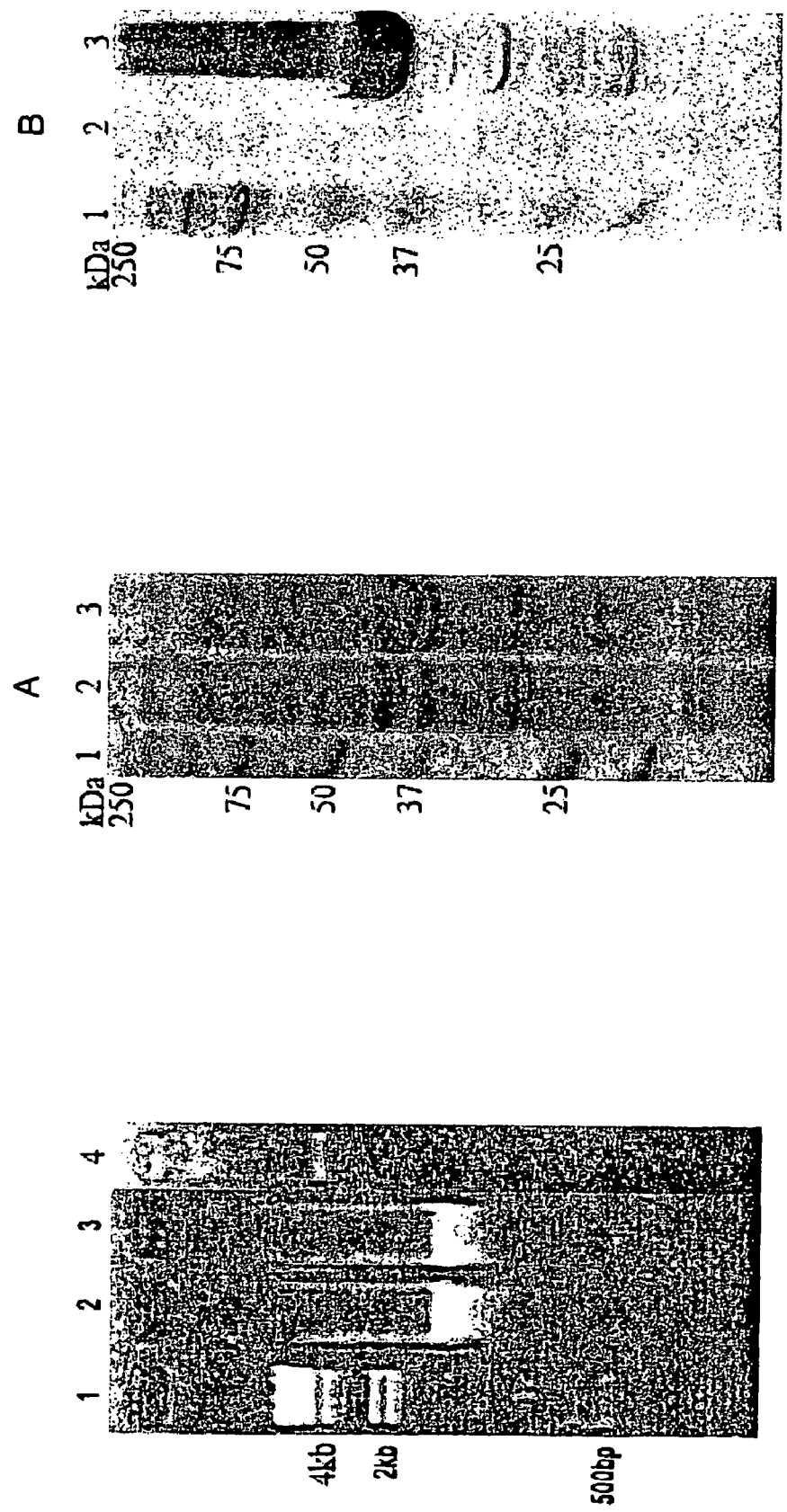

The present invention also provides an antigenic analog, fragment or modification of the polypeptide of FIG. 8 or 9. An antigenic analog, fragment, or modification of said polypeptide is one that generates an immune response in an organism, especially fish, against *A. hydrophila*. Antigenicity of a polypeptide can be evaluated in vitro by, for example, performing a Western blot on the purified polypeptide (for example, an affinity purified polypeptide) using polyclonal antisera from an animal, such as a rabbit that was vaccinated with at least an antigenic portion of the native *A. hydrophila* S-layer 50 kDa protein of the present invention.

Antigenic analogs of the polypeptide according to FIG. 8 or 9 include polypeptides having amino acid substitutions that do not eliminate polypeptide antigenicity in an organism, especially fish. Substitutes for an amino acid may be selected from other members of the class to which the amino acid belongs. For example, nonpolar (hydrophobic) amino acids include alanine, leucine, isoleucine, valine, praline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$.

Fragments of said 50 kDa polypeptide of the invention include polypeptides containing deletions or additions of one or more contiguous or non-contiguous amino acids that do not eliminate the antigenicity of the protein fragment in an organism, especially fish are also contemplated. Fragments of said 50 kDa polypeptide contain at least about six amino acids, preferably at least about 10 amino acids, more preferably at least about 25 amino acids, up to about 50-75 amino acids.

A modified 50 kDa protein of the present invention includes 50 kDa proteins that are chemically and enzymatically derivatised at one or more constituent amino acids, including side chain modifications, backbone modifications, and N- and C-terminal modifications including acetylation, hydroxylation, methylation, amidation, phosphorylation and the attachment of carbohydrate or lipid moieties, cofactors, and the like.

The polypeptides of the present invention can be expressed from an appropriate nucleic acid molecule. The present invention therefore extends to a nucleic acid molecule capable of expressing the polypeptide, antigenic analog, fragment or modification thereof. The nucleic acid may comprise the sequence as shown in FIG. 8 or 9 or an appropriate modification or fragment thereof.

The nucleic acid molecule of the invention can be DNA, RNA, or a combination thereof, and can include any combination of naturally occurring, chemically modified or enzymatically modified nucleotides. The nucleic acid molecule can be equivalent to a polynucleotide fragment encoding the S-layer protein from *A. hydrophila* defined hereinabove, or it can include said polynucleotide fragment in addition to one or more additional nucleotides or polynucleotides. For example, the nucleic acid molecule of the invention can be a vector, such as an expression or cloning vector.

A vector useful in the present invention can be circular or linear, single-stranded or double stranded, and can include DNA, RNA, or any modification or combination thereof. The vector can be a plasmid, a cosmid, or a viral vector, such as a bacteriophage. Preferably, the nucleic acid molecule of the invention takes the form of an expression vector that is capable of expression in an organism or in a cell of the organism, in culture or in vivo. An organism or cell in which the coding sequence of the vector can be expressed can be eukaryotic or prokaryotic, and can be, without limitation, a bacterium, a yeast, an insect, a protozoan, or animals, such as a fish or a mammal. Preferably, the vector is expressible in a fish and/or in a conventional protein expression system, including bacteria, such as *E. coli*, yeast, such as *Pischia pastoris*, mammalian cell culture or insect cells.

When the vector is intended for use in bacterial, yeast, mammalian or insect expression systems, the coding sequences of the vector may be engineered to utilise the conventional genetic code rather than the *A. hydrophila* genetic code that is employed in the native *A. hydrophila* coding sequences.

It should be understood that the nucleic acid molecule of the invention can be single-stranded or double-stranded, and further that a single-stranded nucleic acid molecule of the invention includes a polynucleotide fragment having a nucleotide sequence that is complementary to a nucleotide sequence that encodes said 50 kDa protein or portion thereof according to the invention. As used herein, the term "complementary" refers to the ability of two single stranded polynucleotide fragments to base pair with each other.

Further, a single-stranded nucleic acid molecule of the invention also includes a polynucleotide fragment having a nucleotide sequence that is substantially complementary to a nucleotide sequence that encodes said 50 kDa protein or portion thereof according to the invention, or to the complement of the nucleotide sequence that encodes said 50 kDa protein or portion thereof. Substantially complementary polynucleotide fragments can include at least one base pair mismatch, such that at least one nucleotide present on a first polynucleotide fragment will not base pair to at least one nucleotide present on a second polynucleotide fragment, however the two polynucleotide fragments will still have the capacity to hybridize. The present invention therefore encompasses polynucleotide fragments which are substantially complementary. Two polynucleotide fragments are substantially complementary if they hybridize under hybridization conditions exemplified by 2×SSC (SSC: 150 mM NaCl, 15 mM trisodium citrate, pH 7.6) at 55° C. Substantially complementary polynucleotide fragments for purposes of the present invention preferably share at least about 85% nucleotide identity, preferably at least about 90%, 95% or 99% nucleotide identity. Locations and levels of nucleotide sequence identity between two nucleotide sequences can be readily determined using, for example, CLUSTALW multiple sequence alignment software.

The invention further includes a nucleic acid molecule comprising a polynucleotide fragment that hybridises to at least a portion of the complement of the sequences provided by FIG. 8 or 9 under standard hybridisation conditions, provided that the polynucleotide fragment encodes a polypeptide comprising at least an antigenic portion of the 50 kDa protein of the present invention. Standard hybridisation conditions are exemplified by 2×SSC (SSC: 150 mM NaCl, 15 mM trisodium citrate, pH 7.6) at 55° C.

The present invention further provides a vaccine for use in preventing or controlling disease in fish caused by *A. hydrophila*. The vaccine may be a polypeptide or polynucleotide vaccine. Said polynucleotide vaccine comprises a polynucleotide fragment, preferably a DNA fragment, having a nucleotide sequence encoding an antigenic polypeptide comprising at least an antigenic portion of the S-layer protein of approximately 50 kDa from *A. hydrophila* as shown in FIG. 8 or 9.

The polypeptide vaccine of the invention comprises the 50 kDa protein having amino acid sequence shown in FIG. 8 or 9, an antigenic analog, fragment, or modification of said protein. This type of vaccine is referred to herein as a "protein subunit vaccine" even if it contains the entire 50 kDa protein sequence. The 50 kDa protein or antigenic analog, fragment, or modification thereof for use in the protein subunit vaccine of the invention can be naturally occurring (i.e. isolated from *A. hydrophila*) or recombinant. A protein subunit vaccine of the invention is conveniently administered to fish using bath immersion, ingestion, topical administration, or direct injection, preferably intraperitoneal or intramuscular injection. A protein subunit vaccine formulated for oral administration can contain the polypeptide encapsulated in for example, a biodegradable polymer as described hereinafter. In addition, the protein subunit vaccine can be administered to an animal via a live vector, such as recombinant *Tetrahymena*.

The invention further provides a method for immunising freshwater fish or shellfish against *A. hydrophila* by administering to the fish/shellfish a protein subunit vaccine of the invention.

The amount of protein subunit vaccine to be administered to an animal depends on the type and size of animal, the condition being treated, and the nature of the protein, and can be readily determined by one of skill in the art. In fish, for example, if the protein subunit vaccine is to be injected, the amount per injection is preferably between about 0.1 µg and about 1000 µg per 10 g fish; more preferably it is between about 1 µg and about 100 µg per 10 g of fish. For administration by immersion, the concentration of the protein in the aquatic medium is preferably at least about 10 ng/mL; at most it is preferably about 50 µg/mL, preferably it is less than about 1 µg/mL. For oral administration the amount per dose is preferably between about 0.1 µg and about 100 µg per 10 g fish; more preferably it is between about 1 µg and about 10 µg per 10 g of fish. Conveniently, the protein subunit vaccine may include an adjuvant. Further, one or more boosters are preferably administered at time periods subsequent to the initial administration to create a higher level of immune response in the animal.

In yet another aspect, the vaccine of the invention comprises a fusion protein comprising a carrier polypeptide and said 50 kDa protein of the invention or an analog, fragment, or modification thereof. The 50 kDa protein analog, fragment, or modified protein for use in this aspect of the invention can itself be antigenic or nonantigenic; in embodiments wherein the protein analog, fragment or modified protein is nonantigenic, the carrier polypeptide provides the necessary antigenicity by stimulating the fish's immune system to react to the fusion protein thereby generating an immune response in an organism, especially fish against *A. hydrophila*. A nonantigenic analog, fragment, or modification of the 50 kDa protein thus functions as a hapten. An example of an antigenic carrier polypeptide is keyhole impet hemocyanim (KLH). Conventional fusion constructs between carriers such as glutathione sulfotransferase (GST) and said 50 kDa protein of the invention or antigenic analog, fragment, or modifications thereof are also included as protein subunit vaccines according to the invention, as are fusions of the 50 kDa protein, analog, fragment or modification and an affinity tag such as a polyhistidine sequence. A fusion construct may be preferred for use as a protein subunit vaccine when the antigenic 50 kDa protein analog, fragment, or modification thereof is small. The invention further provides a method for immunising freshwater fish against *A. hydrophila* by administering to the fish a fusion protein vaccine of the invention.

A polynucleotide vaccine optionally further comprises a promoter, such as the CMV promoter, operably linked to the coding sequence for the 50 kDa polypeptide or antigenic fragment thereof (e.g., U.S. Pat. No. 5,780,448, Davis). The polynucleotide may be cloned within a vector such as a plasmid. There are numerous plasmids known to those of ordinary skill in the art useful for the production of polynucleotide vaccines.

Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to affect the animal's reproductive system. A polynucleotide vaccine of the invention can also encode a fusion product containing the antigenic polypeptide and a molecule, such as CTLA-4, that directs the fusion product to antigen-presenting cells inside the host.

Plasmid DNA can also be delivered using attenuated bacteria as delivery system, a method that is suitable for DNA vaccines that are administered orally: Bacteria are transformed with an independently replicating plasmid, which becomes released into the host cell cytoplasm following the death of the attenuated bacterium in the host cell. An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, retroviruses and bacteriophage. Exemplary bacterial vectors include attenuated forms of *Salmonella, Shigella, Edwardsiella ictaluri*, and *Yersinia ruckeri*. Preferably, the polynucleotide is a vector, such as a plasmid, that is capable of autologous expression of the nucleotide sequence encoding said 50 kDa protein or fragment thereof.

In one embodiment, the vaccine is a DNA vaccine comprising a DNA fragment having a nucleotide sequence that encodes a polypeptide having amino acid sequences shown in FIG. 8 or 9, an antigenic analog, fragment, or modified version thereof.

Polynucleotide-based immunisation induces an immune response to an antigen expressed in vivo from a heterologous polynucleotide fragment introduced into the fish. This method can be advantageous over other methods because heterologous nucleic acid expression may continue for a length of time sufficient to induce a relatively strong and sustained immune response without the need for subsequent "booster" vaccinations, as is common when portions of the protein antigen itself have been injected into the animal. A polynucleotide vaccine comprising a polynucleotide fragment having a nucleotide sequence encoding said 50 kDa protein can be administered to a fish using biolistic bombardment, bath immersion, ingestion or direct injection, as described for example, in U.S. Pat. No. 5,780,448 (Davis), preferably intraperitoneal or intramuscular injection. A preferred method of administration is biolistic bombardment, as with a "gene gun". A polynucleotide vaccine formulated for oral administration preferably contains DNA encapsulated in a biodegradable polymer. Examples of a suitable biodegradable polymer include chitosan and homo- or co-polyers of polylactic acid and polyglycolic acid. The invention thus further provides a method for immunising freshwater fish or shellfish as against *A. hydrophila* by administering to the fish a polynucleotide vaccine of the invention, preferably a DNA vaccine.

The amount of polynucleotide vaccine to be administered to an animal depends on the type and size of animal, the condition being treated, and the nature of the polynucleotide, and can be readily determined by one of skill in the art. In fish, for example, if the polynucleotide vaccine is to be injected, the amount per injection is preferably at least about 10 ng; at most it is preferably about 50 µg, more preferably it is less than about 1 µg. If the polynucleotide vaccine is to be administered using a gene gun, the amount per dose is preferably at least about 1 ng; at most it is preferably about 10 µg, more preferably it is less than about 1 µg. For administration by immersion, the concentration of the polynucleotide in the aquatic medium is preferably at least about 10 ng/mL; at most it is preferably about 50 µg/mL, preferably it is less than about 1 µg/mL. For oral administration the amount per dose is preferably at least about 10 µg; at most it is preferably about 10 µg, preferably less than about 1 µg. In some applications, one or more booster administrations of the vaccine at time periods subsequent to the initial administration are useful to create a higher level of immune response in the animal.

The inventors have observed that serum obtained from infected fish isprotective in passive immunisation experiments, but the activity is serotype-specific. On the other hand, fish that are actively immune following exposure to one serotype may be cross-protected against heterologous strains. Thus, in one embodiment, the vaccine of the invention (whether in the form of a protein vaccine or a polynucleotide vaccine) is monovalent in that it is derived from a particular 50 kDa protein from a particular serotype of *A. hydrophila* and effective to treat or prevent infection of the vaccinated species by that serotype. Preferably, the monovalent vaccine contains at least one antigenic determinant that is shared by the 50 kDa protein of different serotypes, such that is also prevents infection by other *A. hydrophila* of other serotypes, thus offering broad protection. In another embodiment, the vaccine of the invention (whether in the form of a protein vaccine or a polynucleotide vaccine) is a combined vaccine or a multivalent vaccine that prevents infection by other *A. hydrophila* of more than one serotype. The combined or multivalent vaccine can contain or encode, for example, a plurality of serotype-specific 50 kDa S-layer proteins or antigenic portions thereof, derived from multiple serotypes of A. hydrophila, or can contain or encode a synthetic or fusion 50 kDa protein containing multiple antigenic determinants that together generate an immune response against multiple serotypes of A. hydrophila.

In one embodiment of the vaccine of the invention, the 50 kDa protein or an antigenic portion, analog or modified version thereof may be linked, for example, at its carboxy-terminus to a further component. The further component may serve to facilitate uptake of the 50 kDa protein or an antigenic portion, analog or modified version thereof, or enhance its immuneginicity/processing. For example, the 50 kDa protein or an antigenic portion, analog or modified version thereof may be linked to at least two molecules of the C3d component of complement, using molecular cloning techniques. Preferably, the 50 kDa protein or antigenic portion, analog or modified version thereof is linked to about three molecules of the C3d component of complement. The C3d molecule can be either homologous or heterologous with respect to the species to be vaccinated. Complement genes have been cloned and characterised in salmonids (J. Lambris et al., *J. Immunol.* 151:6123-6134 (1993); J. Sunyer et al., *Proc. Natl. Acad. Sci USA* 93:8546-8551 (1996)). For vaccinations of fish, the 50 kDa protein or antigenic portion, analog or modified version thereof is preferably linked to a salmonid C3d, such as trout C3d or catfish C3d. In the case of a protein subunit vaccine, the recombinant protein is conveniently expressed in bacteria, then administered to fish. The receptor for C3d, namely CD21, is expressed primarily on B cells and the follicular dendritic cells of lymphoid tissues. In the case of a polynucleotide vaccine, a plasmid encoding a fusion protein that incorporates an 50 kDa protein or antigenic portion, analog or modified version thereof, linked at its carboxy-terminus to at least two molecules of the C3d component is administered to the fish.

The immune-stimulating compositions of the invention may be optionally mixed with excipients or diluents that are pharmaceutically acceptable as carriers and compatible with the active component(s). The term "pharmaceutically acceptable carrier" refers to a carrier(s) that is "acceptable" in the sense of being compatible with the other ingredients of a composition and not deleterious to the recipient thereof. Suitable excipients are well known to the person skilled in the art. Examples include; water, saline (e.g. 0.85% sodium chloride; see Ph. Eur. monograph 2001:0062), buffered saline, fish oil with an emulsifier (e.g. a lecithin, Bolec Mont.), inactivant (e.g. formaldehyde; see Ph. Eur. monograph 1997:0193), mineral oils, such as light mineral oils, alhydrogel, aluminium hydroxide. Where used herein, the term "oil adjuvant" to embraces both mineral oils and synthetic oils. A preferred adjuvant is Montanide ISA 711 (SeppicQuai D'Orsay, 75321 Paris, France) which is a manide oleate in an oil suspension. In addition, if desired, the immune-stimulating composition (including vaccine) may contain minor amounts of auxiliary substances such as wetting or emulsifying agents, pH buffering agents, and/or adjuvants which enhance the effectiveness of the immune-stimulating composition.

Thus the present invention also relates to methods for formulation of such proteins to render them suitable for administration by for example immersion or orally via incorporation into fish food. In one embodiment of the invention pertaining to formulation of the vaccine for the immersion vaccination of fish, the polypeptide or nucleic acids may be packaged within a micro-particulate delivery system, which may include, but is not limited to, latex beads, poly(lactide-co-glycolide) microspheres, atelocollagen "minipellets", bentonite, orporous apatite ceramics including hypoxyapatite (HA) and beta-tricalcium phosphate (TCP).

For example, for an immersion vaccine, an aqueous suspension is preferred. For an oral vaccine a fish oil and lecithin carrier system may be used. For an injection vaccine Montanide ISA711®, Speic at a ratio of 30:70 may be used.

A vaccine composition may be administered as a course of a number of discrete doses over a period of time. For example it may be administered over a period of around 2-21 days.

Vaccination may be repeated at daily, twice-weekly, weekly or monthly intervals. For example a boost vaccination may be administered after the initial dose. For example a boost may be administered at around 4-14 weeks after the vaccination. The initial vaccination and any boost may be carried out using the same or different modes of administration. For example, the initial may be by injection and the boost may be by oral administration. An example regime includes a first vaccination by injection, followed by a course of orally administered boost vaccine, or a booster prior to an expected outbreak. However, it will be appreciated that any suitable route of administration(s) and/or regime(s) may be employed.

In an example embodiment, the polypeptide or polynucleotide may be diluted to a suitable concentration in an enclosed tank containing water as used for the normal culturing of the relevant fish species and fish fry and the fish/fry are immersed in this solution for a period of say, several hours. The fish may then be returned to their normal culturing conditions. With this practice the polypeptides/polynucleotides may enter the gills or digestive tract of the fish and be engulfed by antigen presenting cells and subsequently induce an immune response.

In another embodiment, microparticles containing the polypeptides/polynucleotides are incorporated into a typical fish food preparation and fed to fish in place of ordinary feed. In this method the recombinant proteins will enter the digestive tract stimulating an immune response in systemic or gut-associated lymphoid tissues. This method has the advantage of being suitable for use in netted enclosures where sealed tanks are not available.

Other adjuvants, carriers etc., and modes of administration may be found by referring to Gudding et al (1999) Veterinary Immunology and Immunopathology 72, 203-212.

*Aeromonas hydrophila* is mainly a problem in freshwater, affecting most cultured and wild freshwater fish, although it has been reported in some marine fish, shellfish, amphibians and reptiles. Therefore the species that can be vaccinated with the *A. hydrophila* vaccine is very diverse, and may include animals maintained in aquaculture systems, in public aquaria and by hobbyists, such as the example species listed below.

Abalone *Haliotis discus hannai*; Adriatic sturgeon *Acipenser naccarii*; African catfish *Clarias bartachus*; African cichlid *Nimbochromis venustus*; Amberjack *Seriola dumerili*; American crayfish *Orconectes limosus, Pacifastacus leniusculus, Procambarus .~clarkia*; American plaice *Hippoglossoides platessoides:* Arctic char *Salvelinus alpinus* L.; Atlantic cod *Gadus morhua* L.; Atlantic croaker *Micropogon undulates*; Atlantic menhaden *Brevoortia tyrannus* Latrobe; Atlantic salmon *Salmo salar* L. ; Australian oyster *Saccostrea commercialis*; Ayu *Plecoglossus altivelis*; Balloon molly *Poecilia* spp.; Banana prawn *Penaeus merguiensis*; Barramundi *Lates calcarifer* (Bloch); Bighead carp *Aristichthys nobilis*; Black acara *Cichlasoma bimaculatum*; Black mullet *Mugil cephalus*; Black scraper *Novodon modestus*; Black skirted tetra *Hyphessobrycon* spp.; Blenny *Zoarces viviparous*; Blue fish *Pomatomus saltatrix*; Blue mackerel *Scomber australasicus*; Blue manna crab *Portunus pelagicus*; Blue shrimp *P. (Litopenaeus) stylirostris*; Boney bream *Nematolosa come* (Richardson); Borneo mullet *Liza macrolepis*; Bream *Abramis brama*; Brine shrimp *Artemia*; Brook salmon *Salvelinus fontinalis*; Brook trout *Salvelinus fontinalis* (Mitchill); Brown bullhead *Ictalurus nebulosus* (Lesueur); Brown trout *Salmo trutta*; Brown-spotted grouper *Epinephelus tauvina, E. Coioides*; Bullfrog *Rana catesbeiana*; Burnett salmon *Polydactylus sheridani* (Macleay); Canadian shrimp *Lismata amboiens*; Carp *Cyprinus carpio* L.; Catfish *Clarius batrachus* L.; Caucasian carp *Carassius carassius*; Chanchito *Chichlasoma facetum* (Jenyns); Channel catfish *Ictalurus punctatus* (Rafinesque); Chinook salmon *Oncorhynchus tschawytscha*; Chub *Leuciscus cephalis*; Chum salmon *Oncorhynchus keta* (Walbaum); Cichlid *Oreochromis mossambicus*; Clam *Tapes philippinarum*; Cod *Gadus morhua*; Coho salmon *Oncorhynchus kisutch*; Common carp *Cyprinus carpio* L.; Common snook *Centropomus undecimalis*; Common wolf-fish *Anarhichas lupus*; Coral prawn *Metapenaeopsis* spp.; Crucian carp *Carassius carassius*; Cutthroat trout *Salmo clarki*; Cuttle fish *Sepia officinalis*; Cuvier Plaice *Pleuronectes platessa*; Dab *Limanda limanda*; Dace *Leuciscus leuciscus* L.; Damselfish *Chromis punctipinnis*; Pomacentridae, Amphiprion clarkii (Bennett), *Amblyglyphidodon curacao* (Bloch); Danio *Danio devario*; Discus fish *Symphysodon discus, S. aequifasciatus*; Dolphin fish *Coryphaena hippurus* L.; Eastern freshwater cod *Maccullochella ikei*; Eastern mosquitofish *Gambusia holbrooki* J; Eastern painted turtle *Chrysemys picta picta*; Eel *Anguilla japonica, A. reinhardtii; A. anguilla, A. Rostrata*; European crayfish *Astacus leptodactlus, A. pachypus, A. torrentium, A. astacus, Austropotamobius pallipes*; European sea bass *Dicentrarchus labra*; Fairy shrimp *Branchipus schaefferi* (Fisher), *Chirocephalus diaphanus* (Prevost), *Streptocephalus torvicornis* (Waga); Farmed mussel *Perna perna*; Fathead minnow *Pimephales promelas*; Flat-tailed mullet *Liza dussumieri* (Valenciennes); Firemouth cichlid *Cichlasoma meeki*; Flounder *Paralichthys olivaceus, Platichthys flesus*; Four bearded rockling *Enchelyopus cimbrius* L.; Freshwater cod (Australian native) *Maccullochella* spp.; Freshwater prawn *Macrobranchium rosenbergii*; Golden shiner *Notemigonus crysoleucas* (Mitchell); Goldfish *Carassius auratus* L; Goldsinny wrasse *Ctenolabrus rupestris*; Gourami (three-spot) *Trichogaster trichopterus*; Grass carp *Ctenopharyngodon idella*; Grayling *Thymallus thymallus* L; Greater weever *Trachinus draco*; Green frog *Rana clamitans*; Green knife fish *Eigemannia virescens*; Green moray eel *Gymnothorax funebris*; Green sturgeon *Acipenser medirostris*; Greenback flounder *Rhombosolea tapirina*; Grouper *Epinephelus guaz, E. coioides*; Guppy *Poecilia reticulata* (Peters), *Lebistes reticulates*; Haddock *Melanogrammus aeglefinus* L.; Halibut *Hippoglossus hippoglossus*; L Herring *Arripis georgianus*; Horse mackerel *Trachurus trachurus*; Iberian toothcarp *Aphanius iberus*; Japanese abalone *Sulculus diversicolor supratexta*; Japanese medaka *Oryzias latipes*; Jewel tetra *Hyphessobrycon callistus* (Boulenger); King prawn *Penaeus latisulcatus*; Knife fish *Gymnotus carapo*; Lake trout *Salmo trutta m lacustris, Salvelinus namaycush* Walbaum; Largemouth bass *Micropterus salmoides*; Leopard frog *Rana pipiens*; Living dace *Tribolodon hakonensis* Gunther; Loach *Misgurnus anguillicaudatus* Cantor; Lobster *Homarus gammarus* L; Local mussel *Mutilus edulis* Longtom *Tylosurus macleayanus* (Ogilby); Mackerel *Scomber-scombrus*; Manila clam *Tapes philippinarum, T. decussatus, Ruditapes philippinarum*; Masu salmon *Oncorhynchus masou*; Menhaden *Brevoortia patronus*; Minnow *Phoxinus phoxinus* L.; Molly *Poecilia velifera* (Regan); Mud crab *Scylla serrata*; Mullet *Mugil cephalus*; Murray cod *Maccullochella peeli:* Mussel *Prothothaca jedoensis, Mytilus edulis, Mytilus galloprovincialis*; Mussel (Far-eastern) *Crenomytilus grayanus, Patinopecten yessoensis*; Neon tetra *Paracheirodon innesi, Hyphessobrycon innesi*; North-east Atlantic mackerel *Scomber scombrus*; Northern pike *Esox lucius* L.; Octopus *Octopus vulgaris, O. joubini*; One-spot bream *Diplodus sargus*; Ornamental fish *Pterophyllum scalare*; Oscar *Astronotus ocellatus; Apistogramma ocellatus*; Oyster *Ostrea edulis; Crassostreae virginica*; Pacific herring *Clupea harengus palla~i;'* Pacific oyster *Crassostrea gigas*; Pacific salmon *Oncorhynchus* spp.; Pacific staghorn sculpin *Leptocottus armatus*; Pacific white shrimp *Penaeus vannamei*; Paradise fish *Macropodus opercularis* (L.); Pejerrey *Odonthestes bonariensis*; Perch *Perca fluviatilis*; Pickerel frog *Rana palustris*; Pike *Esox lucius*; Pilchard *Sardinops neopilchardu*; Pink salmon *Oncorhynchus gorbuscha*; Pink snapper *Chrysophrys unicolor*; Pinkfish *Lagodon rhomboids*; Pirarucu *Arapaima gigas*; Pompanos *Trachinotus carolinus* L; Rabbitfish *Siganus rivulatus* (ForsskAl); Rainbow trout *Oncorhynchus mykiss* (Walbaum); Red abalone *Haliotis rufescens;* Red algae *Jainia* spp.; Red claw crayfish *Cherax quadricarinatus* L.; Red drum, Redfish *Sciaenops ocellatus;* Red sea bream *Pagrus major;* Red swamp crawfish *Procambarus clarkia;* Red-eared slider turtle *Chrysemys scripta elegans;* Redtail catfish *Phractocephalus hemiliopterus;* Regan Signal crayfish *Pacifastacus leniusculus;* Roach *Rutilus rutilus* L.; Rohu *Labeo rohita;* Rosy barb *Puntius conchonius;* Rudd *Scardinius erythrophthalmus;* Sablefish *Anoplopoma fimbria* (Pallas); Saltwater crocodile *Crocodylus porosus;* Sand eel *Ammodytes lancea* (Cuvier), *Hyperoplus lanceolatus* (Lesauvege); Sand lance *Ammodytes personatus* Girard; Sand whiting *Sillago ciliata* Cuvier; Saratoga *Scleropages leichardii;* Sardine *Sardinops melanostictus, Sardinops sagnax;* Scallop *Pecten maximus, Argopecten purpuratus;* Scaly mackerel fish *Amblygaster postera;* Sea bream *Pagrus major, Evynnisjaponicus, Sparzrs aurata, Acanthopagrus latus;* Sea catfish *Arius felis;* Sea horse *Hippocampus angustus, H. barbouri, H. whitei, H. kuda;* Sea mullet *Mugil cephalus* L.; Sea trout *Salmo trutta m. trutta* L.; Sea turtle *Chelonia mydas;* Sea-urchin *Paracentrotus lividu;* Sepiolid squid *Euprymna scolopes;* Shorted halibut *Eopsetta grigorjewi;* Shubunkin *Carassius* spp.; Siamese fighting fish *Betta splendens;* Silver black porgy *Acanthopagrus cuvieri, Pyoscelis papua,;* Silver bream *Acanthopagrus butcheri, A. australis* (Owen); Silver bream *Blicca bjoerkna;* Silver carp *Hypophthalmichthys molitrix* Valenciennes; Silver molly *Poecilia* spp.; Silver mullet *Mugil curema* Valenciennes, *Mugil cephalus* L.; Silver perch *Bidyanus bidyanus* (Mitchell); Silver trout *Cynoscion nothus;* Small abalone *Haliotis diversicolor supertexta;* Smallmouth bass *Micropterus dolomieui;* Snakehead fish *Channa striatus; Ophicephalus punctatus, O. striatus;* Snub-nose garfish *Arrhamphus sclerolepsis* (Gunther); Sockeye salmon *Oncorhynchus nerka* (Walbaum); Softshell clam *Mya arenaria;* Sole *Solea solea;* South African abalone *Haliotis midae;* South American sidenecked turtle *Podocnemis unifelis;* Spanish mackerel *Scomber japonicus;* Spanner crab *Ranina ranina;* Spiny softshelled turtle *Trionyx spinner;* Spot *Leiostomus xanthurus;* Spotted moray eel *Gymnothorax moringa;* Spotted wolf-fish *Anarhichas minor;* Squid *Loligo pealei, Sepiola, T euthoidea;* Starfish *Asterias rubens;* Stingray *Dasyatis pastinaca;* Striped bass *Morone saxatilis* (Walbaum), *M. chrysops;* Striped mullet *Mugil cephalus;* Striped-neck musk turtle *Sternotherus minor peltifer;* Sturgeon *Acipenser naccari;* Sunfish *Mola mola;* Tasmanian lobster *Jasus novaehollandiae;* Tiger Frog *Rana tigrina;* Tilapia *Oreochromis niloticus, O. aurus;* Sarotherodon aureus (Steindachner); *Tilapia nilotica, Tilapia aurea, Tilapia mosambica;* Tom cod *Gadus microgadus;* Tropical shrimp *Stenopus hispidus;* Trout cod *Maccullochella macquariensis;* Turbot *Scophthalmus maximus* L.; Turtle *Dermochelys coriacea; Pseudemis scripta;* Viviparous blenny *Zoarces viviparus;* Western rock lobster *Panulirus cygnus;* White catfish *Ictalurus catus* L.; White clawed crayfish *Austropotamobius pallipes;* White leg shrimp *P. (Litopenaeus) vannamei;* White perch *Roccus americanus, Morone americanus* (Gremlin); Whitefish *Coregonus* spp.; Whitespotted rabbitfish *Siganus canaliculatus;* Whiting *Merlangius merlangus;* Wrasse *Labrus berggylta;* Yellow bass *Morone mississippiensis;* Yellow perch *Perca flavescens;* Yellowfin bream *Acanthopagrus australis* (Owen); Yellowtail *Seriola quinqueradiata, S. lalandi;* Zealand mussel *Perna canaliculus;* Zebra danio *Brachydanio rerio*.

The goal of vaccination against *A. hydrophila* infection is to elicit a population of lymphocytes, which upon subsequent exposure to the parasite proliferate and produce antibodies and/or effector cells specific to the parasite, resulting in protection against lethal infections. A vaccine effective for the prevention of *A. hydrophila* infection in fish is thus one which elicits the production of protective antibodies in a fish exposed to said vaccine. Those protective antibodies will prevent lethal infection of the vaccinated fish upon challenge with *A. hydrophila*. In the present invention, protective antibodies generated in the fish are specific for *A. hydrophila* 50 kDa S-layer proteins of the present invention. Fish that can be immunised include ornamental and food fish.

The present invention further includes monoclonal or polyclonal antibodies, whether derived from fish, rodents, mammals, avians, or other organisms, that bind to the 50 kDa proteins described herein, including antigenic analogs, fragments and modifications thereof. Production and isolation of monoclonal and polyclonal antibodies to a selected polypeptide sequence is routine in the art see for example "Basic methods in Antibody production and characterisation" Howard & Bethell, 2000, Taylor & Francis Ltd. Such antibodies may be used in diagnostic procedures, as well as for passive immunisation.

Sera from immune fish is known to confer passive immunity against both viral and bacterial pathogens when injected into non-immune fish (Hedrick et al. *Trans. Amer, Fish Soc.* 116: 277-281 (1987); Viele et al. *J. Fish Biol.* 17:379-386 (1980)) and thus, sera from animals immunised with a polypeptide or polynucleotide according to the present invention, may be of use.

Additionally, knowledge of the 50 kDa protein nucleotide and amino acid sequences set forth herein also opens up new possibilities for detecting, diagnosing and characterising *A. hydrophila* in fish populations. For example, an oligonucleotide probe or primer based on a conserved region of the 50 kDa protein can be used to detect the presence of the 50 kDa protein in a fish or in water, and an oligonucleotide probe or primer based on a less conserved region can be used to identify a specific *A. hydrophila* serotype. The invention therefore includes methods for detecting and characterising *A. hydrophila*, for example in aquaculture facilities.

One aspect of the present invention relates to DNA construct comprising a replicable expression vector and nucleic acid encoding the 50 kDa protein or analog, fragment or modified version thereof.

Expression vectors for the production of the molecules of the invention include plasmids, phagemids, viruses, bacteriophages, integratable DNA fragments, and other vehicles, which enable the integration of DNA fragments, into the genome of the host. Expression vectors are typically self-replicating DNA or RNA constructs containing the desired gene or its fragments, and operably linked genetic control elements that are recognised in a suitable host cell and effect expression of the desired genes.

These control elements are capable of effecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector containing cells.

Plasmids are the most commonly used form of vector but other forms of vectors which serve an equivalent function and which are, or become, known in the art are suitable for use herein. See, e.g., Pouwels et al. Cloning Vectors: a Laboratory Manual (1985 and supplements), Elsevier, N.Y.; and Rodriquez, et al. (ads.) Vectors: a Survey of Molecular Cloning Vectors and their Uses, Buttersworth, Boston, Mass (1988), which are incorporated herein by reference.

In general, such vectors contain in addition specific genes, which are capable of providing phenotypic selection in transformed cells. The use of prokaryotic and eukaryotic viral expression vectors to express the nucleic acid sequences coding for the recombinant proteins of the present invention are also contemplated.

The vector is introduced into a host cell by methods known to those of skill in the art. Introduction of the vector into the host cell can be accomplished by any method that introduces the construct into the cell, including, for example, calcium phosphate precipitation, microinjection, electroporation or transformation. See, e.g., Current Protocols in. Molecular Biology, Ausuble, F.M., ea., John Wiley & Sons, N.Y. (1989).

Another aspect relates to a host cell transformed with any one of the nucleic acid constructs of the present invention. Suitable host cells include prokaryotes, lower eukaryotes, and higher eukaryotes. Prokaryotes include gram negative and gram positive organisms, e.g., *E. coli* and *B. subtilis*. Lower eukaryotes include yeast, *S. cerevisiae* and *Pichia*, and species of the genus *Diclyostelium*.

"Host cell" as used herein refers to cell which can be recombinantly transformed with vectors constructed using recombinant DNA techniques.

A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cells would be obtained by culturing the cells under conditions which require the induced phenotype for survival. However, the use of plasmids containing such drug resistance markers when administered directly to a fish to be treated is not desired—plasmids lacking such drug resistance markers are preferred.

The host cells according to the present invention are capable of producing a biologically active protein or protein fragment of the invention. Such protein or protein fragment is encoded by the nucleic acid sequence of the invention and is capable of eliciting in an animal protective immunity against a specific adenoviral pathogen.

A process for the production of the recombinant protein or peptide of the invention is also within the scope of the invention. The process comprises the steps of (a) transforming a host cell with the nucleotide sequence of the invention or transfecting a host cell with a nucleic acid construct of the invention; (b) culturing the cells obtained in (a) under conditions in which expression of the protein takes place; and (c) isolating the expressed recombinant protein or peptide from the cell culture or/and the culture supernatant.

The polypeptide may be partially purified from the host before being used as a vaccine. Where the polypeptide is secreted from the host cell, the cells may be separated from the media by centrifugation, the cells being pelleted and the media being the supernatant. In such a situation, the supernatant, which contains the secreted polypeptide, may be used directly as a vaccine, or in a vaccine composition. Alternatively, the polypeptide may be partially purified from this supernatant, for example using affinity chromatography.

The method may further comprise admixing the partially purified polypeptide with another component, such as another polypeptide and/or an adjuvant, diluent or excipient.

Vaccines may contain bacterial antigens used to control other diseases i.e. vaccine composition may be included within a multivalent vaccine which includes antigens against other diseases of fish.

In a still further aspect the present invention provides a fish population which has been treated or immunised with a vaccine or composition described elsewhere herein.

DETAILED DESCRIPTION

The present invention will now be further described by way of example and with reference to the Figures which show:

FIG. 1: Antibody response of common carp against different isolates of *A. hydrophila* determined by ELISA expressed as an absorbance at 450 nm. All sera were diluted 1:512.

Figure 2:
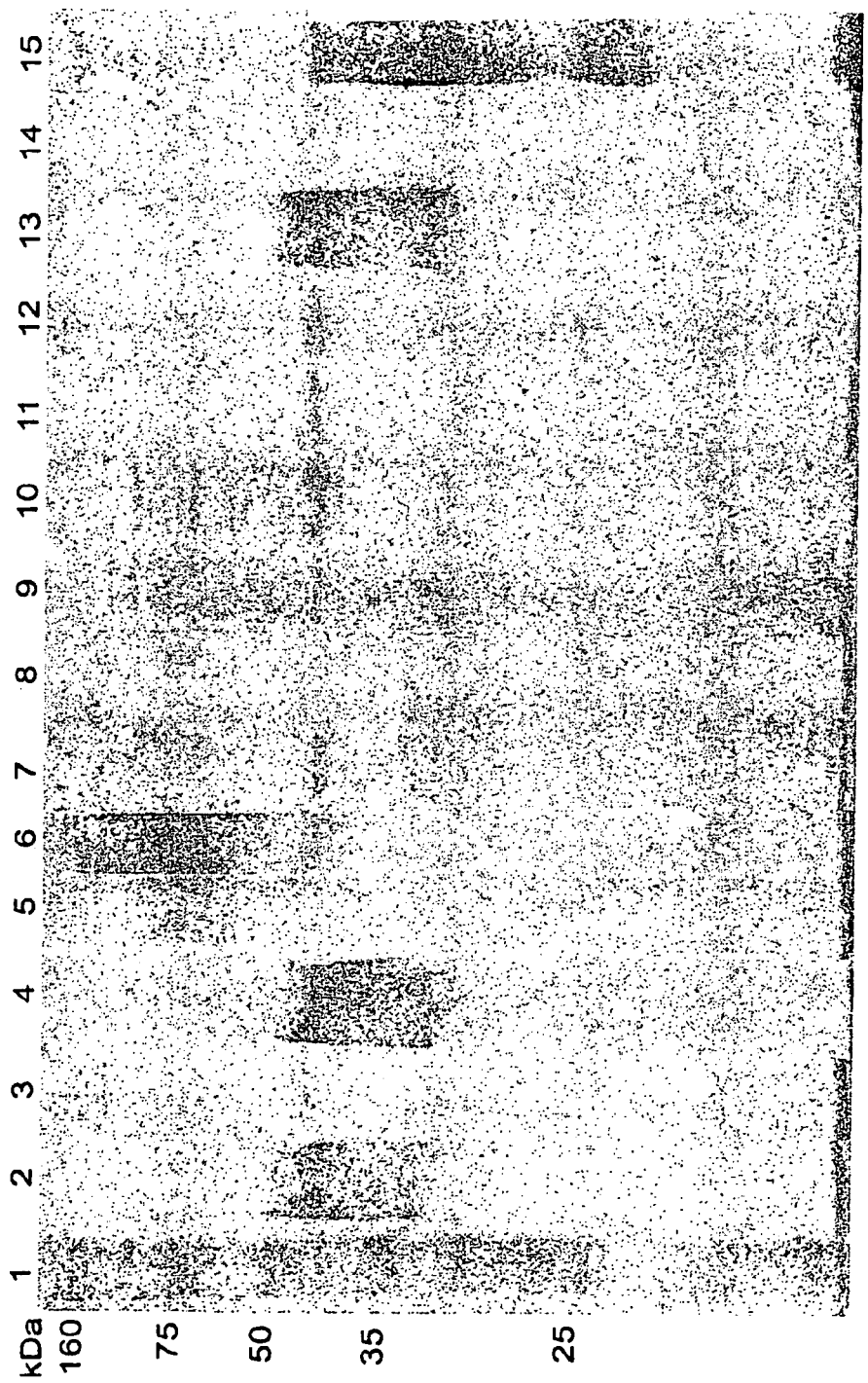

FIG. 2: Western blot analysis of different whole cell preparations of *A. hydrophila* against pooled serum from common carp infected with 6 different *A. hydrophila* isolates. Lanes: (1) Standard marker; (2) T4; (3) 98141; (4) Hh; (5) Vds; (6) Catla; (7) C24li; (8) 2D20; (9) 3D14; (10) 2N14; (11) 98140; (12) 98139; (13) B2/12; (14) Fld75; (15) Calf.

Figure 3:
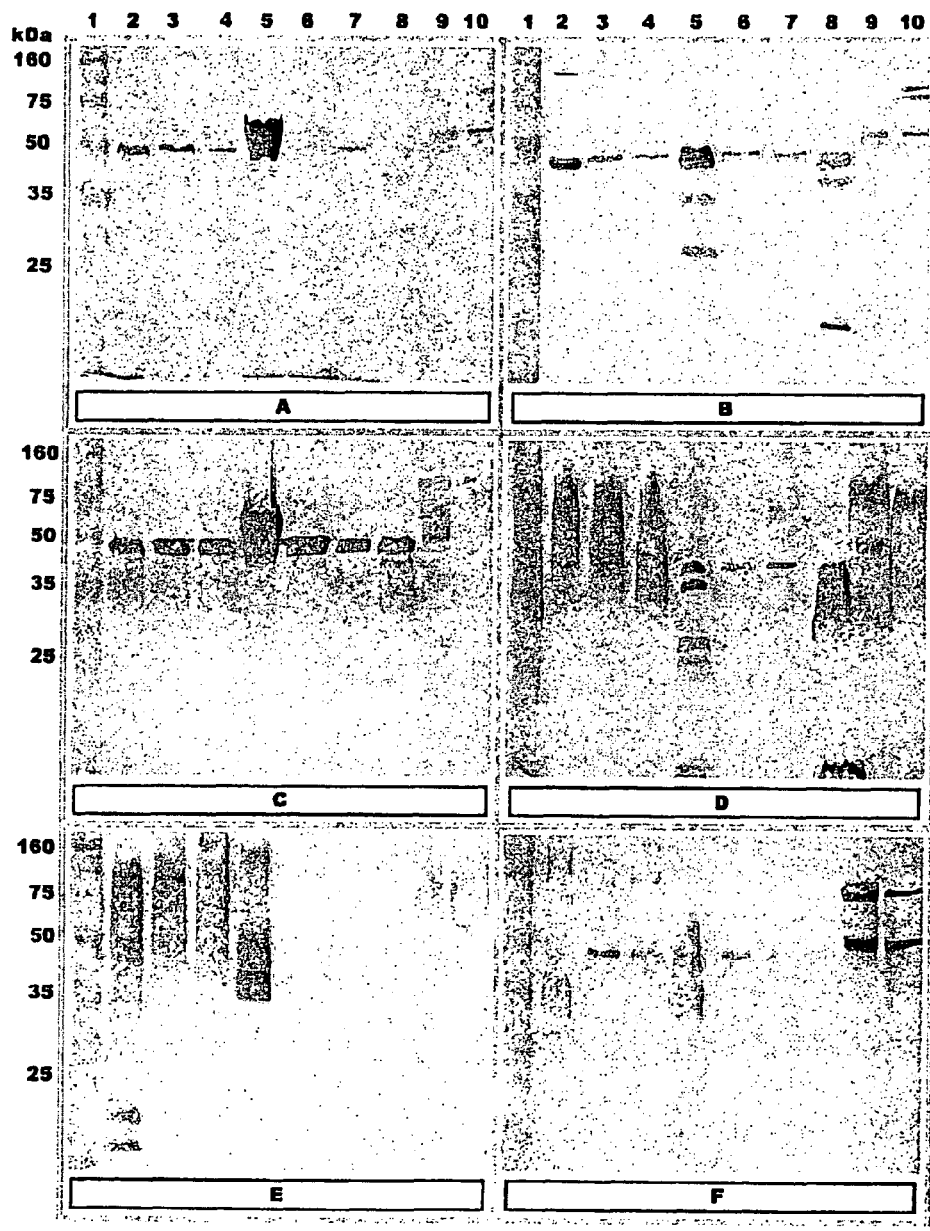

FIG. 3: Western blot analysis of different preparations of 6 *A. hydrophila* isolates screened with serum raised against corresponding *A. hydrophila* isolates in common carp. (A) T4, (B) 98141, (C) Hh, (D) Vds, (E) Catla, (F) C24li. Lanes: (1) Standard marker; (2) WC in vitro; (3) WC in vivo 25 kDa; (4) WC in vivo 100 kDa; (5) OMP in vitro; (6) OMP in vivo 25 kDa; (7) OMP in vivo 100 kDa; (8) ECP in vitro; (9) ECP in vivo 25 kDa; (10) ECP in vivo 100 kDa.

Figure 4:
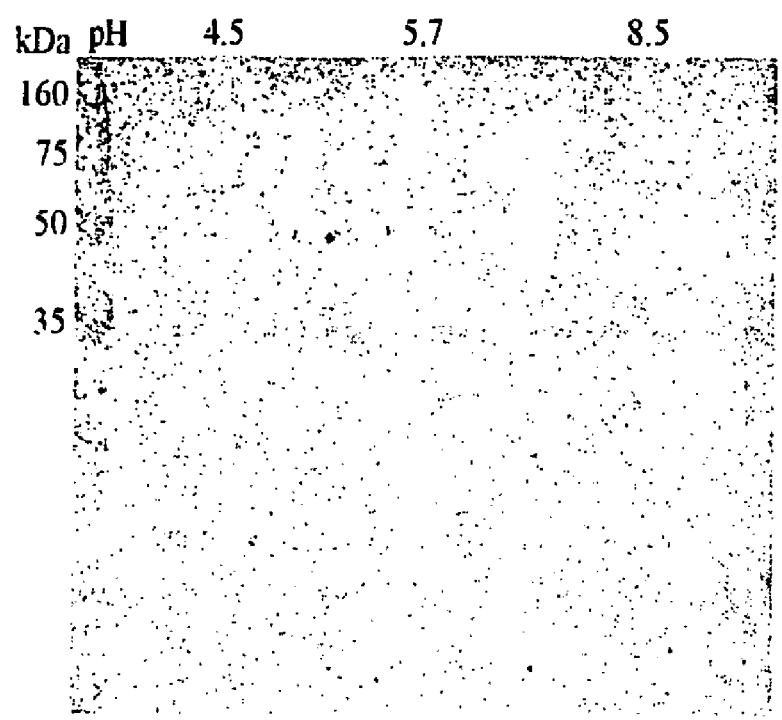

FIG. 4: 2D Western blot analysis of whole cell preparation of *A. hydrophila* T4 isolate screened with antibody from common carp infected with *A. hydrophila* T4 isolate.

Figure 5:
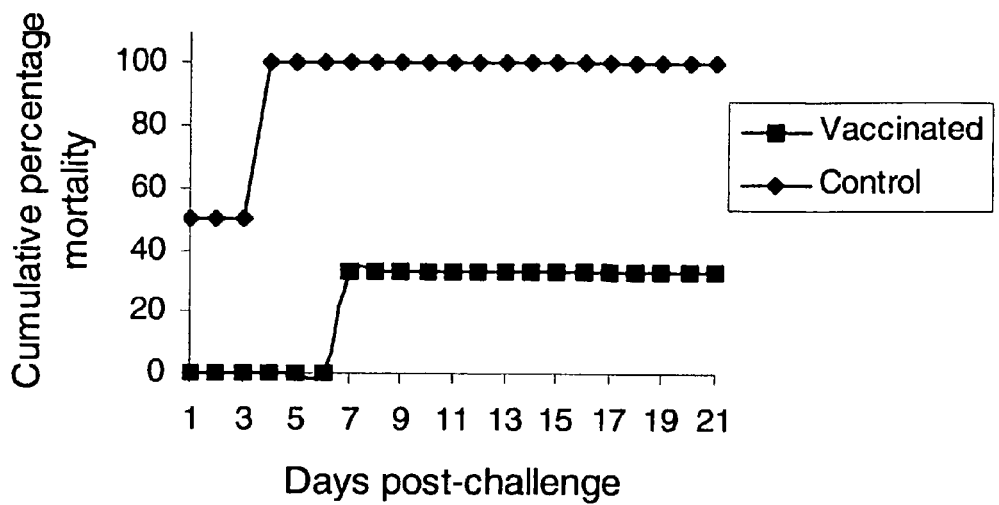

FIG. 5: Cumulative percentage of goldfish mortality in preliminary vaccination trial FIG. 6: MALDI-TOF MS spectrum showing the peptide profiles of 50 kDa band FIG. 7: Nucleic and amino acid sequences of *A. hydrophila* S-layer protein (Nucleic acid sequence: SEQ ID NO:1; amino acid sequence: SEQ ID NO:2).

FIG. 8: Genomic sequences of *A. hydrophila* isolate T4 (Nucleic acid sequence: SEQ ID NO:3; amino acid sequence: SEQ ID NO:4).

FIG. 9: Amplification of the S-layer gene of *A. hydrophila* isolate T4 shown on a 1% agarose gel. Lanes: (1) Standard marker; (2) S-layer protein gene; (3) purified S-layer protein gene; (4) pQE60 vector carrying S-layer protein gene.

FIG. 10: Expression of S-layer protein of *A. hydrophila* with *E. coli* WC protein. (A) 12% SDS-PAGE stained with Coomassie blue, (B) Western blot of protein using an anti-histidine tag antibodies. Lanes: (1) Standard protein marker; (2) WC preparation of recombinant *E. coli* without IPTG induction; (3) WC preparation of recombinant *E. coli* with IPTG induction showing S-layer protein.

Figure 11:
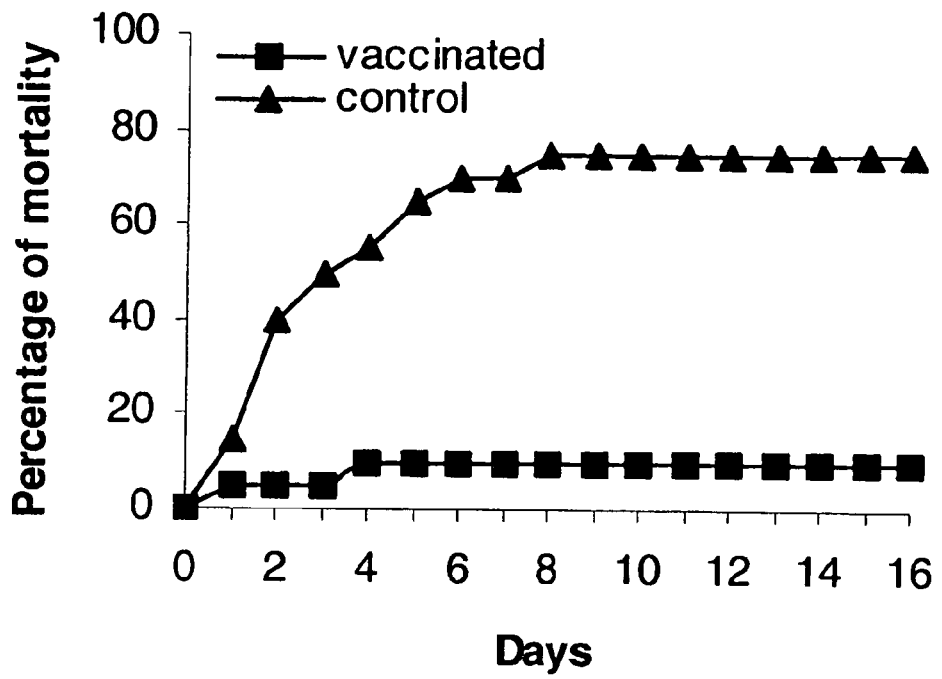
Figure 11:
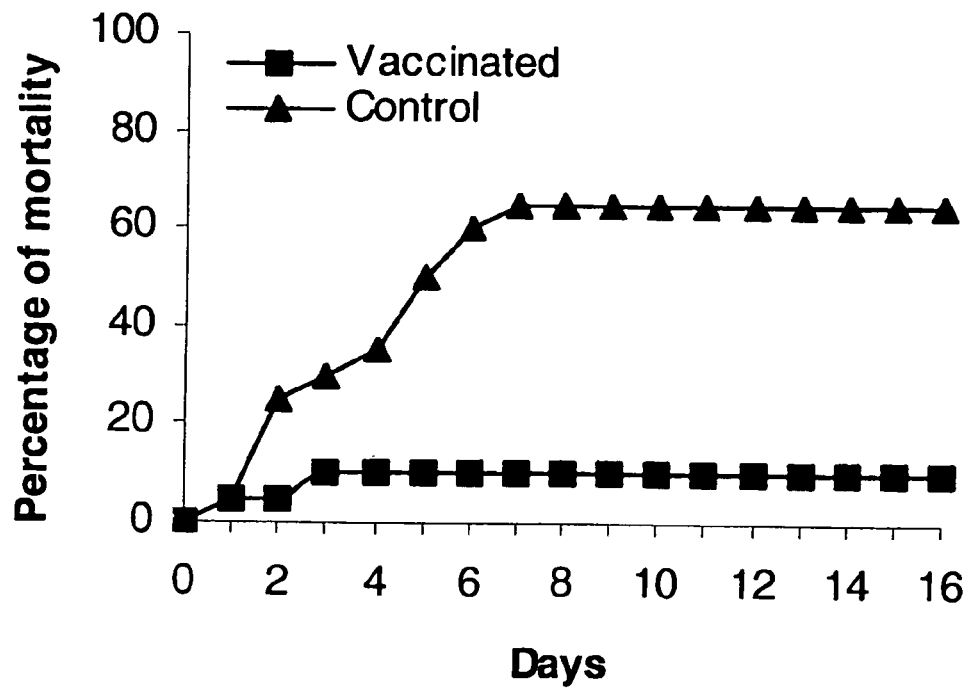
Figure 11:
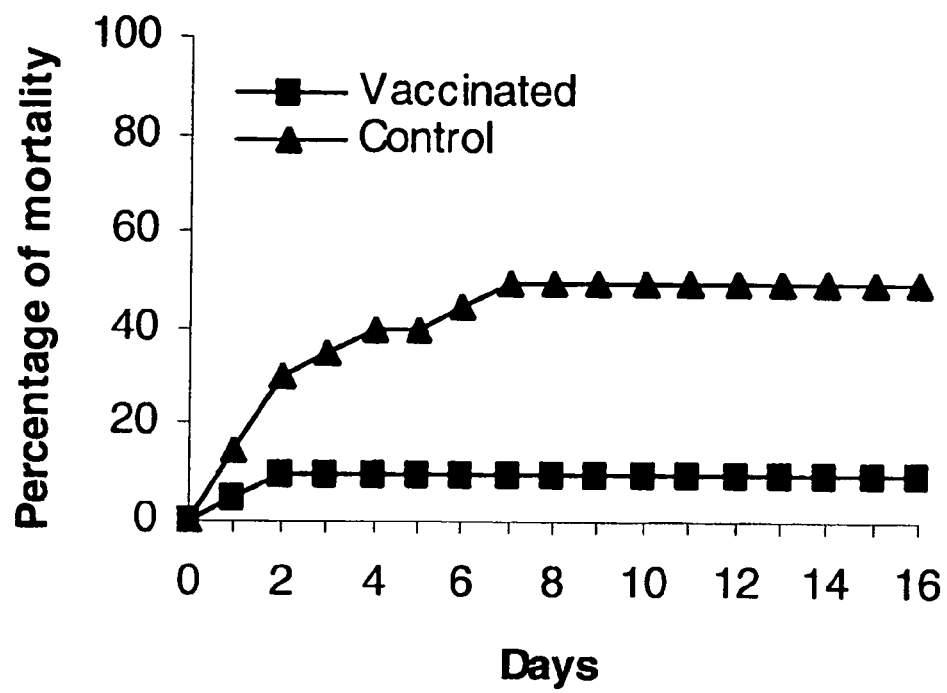
Figure 11:
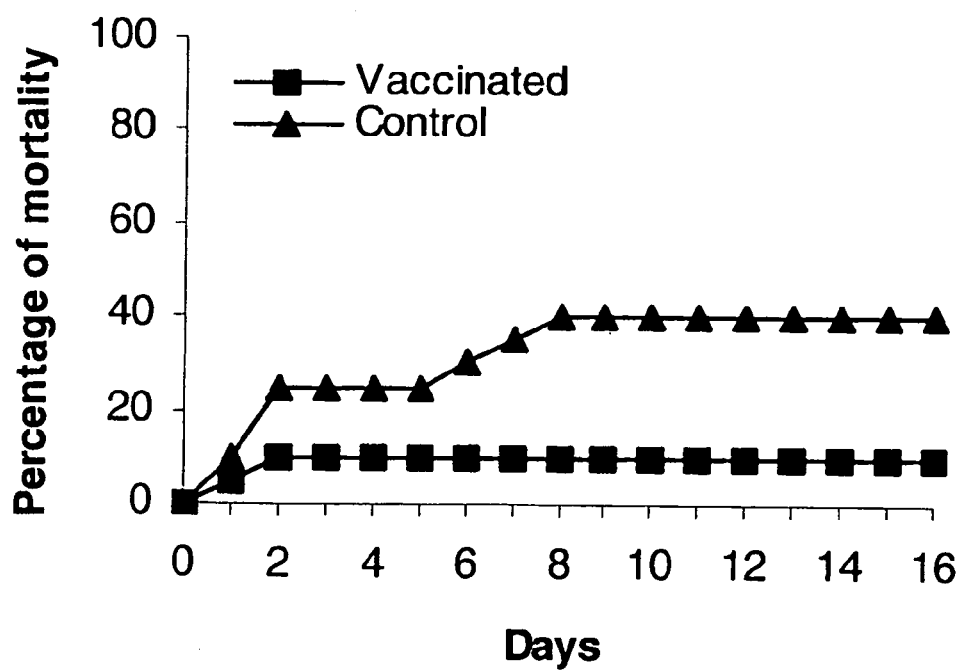
Figure 11:
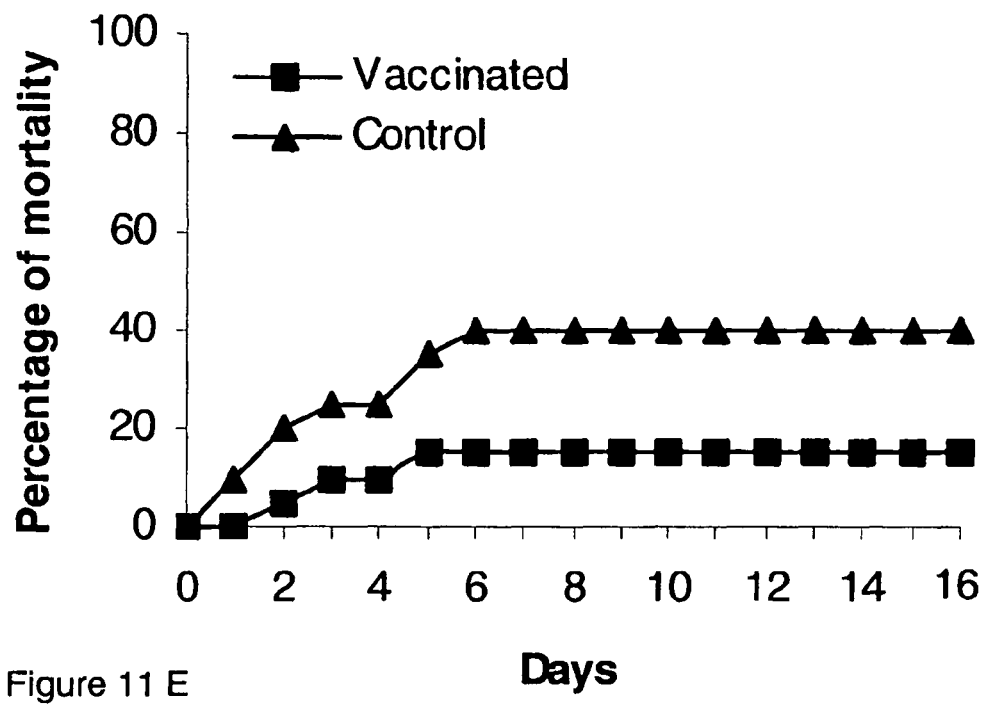
Figure 11:
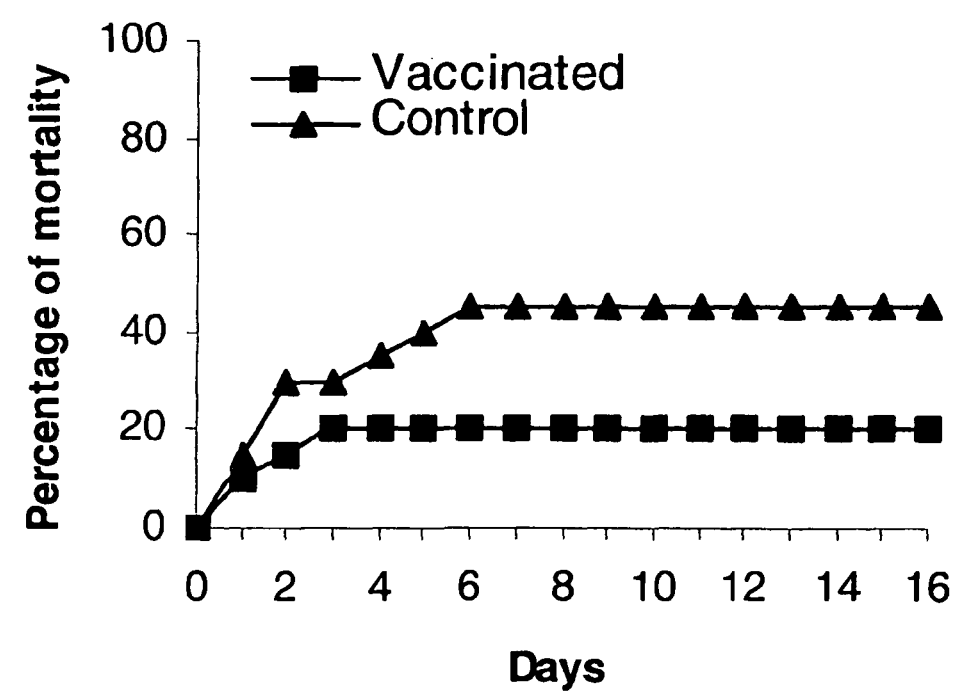

FIG. 11: Cumulative percentage mortality of carp vaccinated with recombinant S-layer protein and challenged with *A. hydrophila* isolates. (A) T4, (B) Hh, (C) 98140, (D) 98141, (E) Vds, (F) B2/12.

MATERIALS AND METHODS

Antibody Response of Common Carp to *A. Hydrophila*

Four virulent strains; T4, 98141, Hh, Vds and two avirulent strains; Catla and C24li of *A. hydrophila* were used (Table 1).

TABLE 1

| Isolate | Fish species | Country/date | Comments |
|---|---|---|---|
| T4 | Rohu (*Labeo rohita*) | Bangladesh (1994) | From an Epizootic Ulcerative Syndrome (EUS) lesion |
| 98141 | Black shark | Ayuthaya | From a Haemorrhagic lesion |
| 98140 | (*Morulius* | Province, Thailand | |
| 98139 | *Chrysophekadion*) | (1998) | |
| Hh | Hedgehog (*Erinaceus Europaeus*) | Institute of Aquaculture, Scotland | — |
| Vds | Catfish (*Ictulurus puctatus*) | India | From an EUS lesion |
| Catla | Catla (*Catla catla*) | India | From heart blood |
| C24li | African catfish, (*Clarias gariepinus*) | Aquatic Animal Health Research Institute, Thailand | — |
| 2D20 | Frog | Asia | — |
| 3D14 | (*Rana rugulosa*) | | — |
| 2N14 | | | — |
| F1d 75 | | | — |
| B2/12 | unknown | Bangladesh | — |
| Calf | unknown | Institute of Aquaculture, Scotland | — |

Common carp (average weight 30 g) were maintained in 6 separate glass tanks. The fish were anesthetized and injected intraperitoneally (IP) with 0.1 ml PBS containing $1 \times 10^6$ viable *A. hydrophila*. Each strain was injected into 24 fish and an additional 24 fish were injected with phosphate buffered saline (PBS) as controls. After injection, the fish were supplied with re-circulating water that had been passed through a sedimentation tank, drum filter, biofilter and ultraviolet (UV) radiation. The temperature of the tank water was maintained at $20 \pm 1°$ C. Blood samples were taken 3, 9, 12 and 21 days post-injection and pre-injection bleeds were taken from six fish. Blood was stored overnight at 4° C. and the serum collected by centrifuging at 2000×g for 5 min. The serum was stored at −20° C. until further analysis.

Western Blot

Western blot analysis was performed using fish anti-sera as per the method outlined by Wiens et al. (1990: with modifications).

Western Blot Using Common Carp Antibody

Western blot analysis was carried out for the 14 *A. hydrophila* isolates shown in Table 1 using pooled common carp serum raised against six isolates of *A. hydrophila* strains (T4, 98141, Hh, Vds, Catla and C24li). Different preparations of the bacterium (L e. Whole cell (WC), outer membrane protein (OMP) and extracellular products (ECP)) prepared from these 6 isolates of *A. hydrophila* grown either in vitro or in vivo were screened by Western blot with each of the 6 anti-sera raised against different isolates of *A. hydrophila*.

The bacterial preparations described above were subjected to 12% SDS-PAGE and the resolved antigens transferred to nitrocellulose membranes (@60 V for 1 h). The nitrocellulose membranes were blocked using 2% (w/v) casein for 1 h at 20-22° C. The membranes were washed three times (Tris buffered saline containing 0.1% (v/v) Tween-20: TTBS/5 min per wash) and then incubated overnight in the common carp anti-serum diluted 1/10 in Tris buffered saline (TBS). Membranes were again washed and incubated with an anti-carp IgM monoclonal antibody (Aquatic Diagnostics Ltd, Stirling, UK) for 2 h. The membranes were washed and incubated with anti-mouse IgG-HRP (Sigma, Missouri, USA) for 1 h. The blots were developed by adding chromogen and substrate solution (2 ml of 4-chloro-naphthol solution with 10 mls of PBS and 10 µl of $H_2O_2$) until bands were observed.

2D SDS-PAGE Western Blot Using Common Carp Antibody

The antigenic profile of WC preparation of isolate T4 grown in vitro was screened using 2D SDS-PAGE and Western blotting with anti-serum (raised for T4 isolate) from common carp.

Assessing the Levels of Protection of a 50 kDa Protein in Goldfish against *A. Hydrophila* Challenge: Preparation of the Antigen.

Volumes (100 µl) of sample were subjected to 12% SDS PAGE. The gels were run for between 5-6 h at 250 V/130 mA. On completion the 50 kDa band was cut from the gel and finely chopped. These were placed in tubes containing 300 µl SDS-PAGE reservoir buffer a blotting paper disk and a porous polyethylene plug. The tip of the tube was cut and placed into a 1.5 ml centrifuge tube containing 300 µL of 4× SDS-PAGE reservoir buffer. The tubes were then placed into an electroluter and subjected to 50 V at 0.5 mA and a reverse run at 50 V for 5 sec at the end. The eluted protein was collected and the reservoir buffer removed using a 10,000 MW cut-off spin concentrator. The concentration of protein was determined. The presence of the 50 kDa protein was confirmed by SDS-PAGE and Western blot.

Immunisation of Goldfish with the Electro-Eluted 50 kDa Protein

For preliminary vaccination, four goldfish weighing around 30-40 g were injected IP with 200 µL of suspension having 12.3 µg of 50 kDa protein in 60 µL of PBS and 140 µL of montanide adjuvant. Another four fish were also injected with PBS to serve as controls. All the fish were challenged with *A. hydrophila* 31 days post-vaccination and sacrificed 21 days after challenge as described above. Samples were taken from their kidneys. The relative percentage survival (RPS) was calculated using the following formula (Ellis, 1988).

$$RPS = 1 - \frac{\% \text{ vaccinated mortality}}{\% \text{ control mortality}} \times 100$$

In addition, two goldfish weighing 30-40 g were injected IP with 200 µL of antigen (i.e. 12.3 µg 50 kDa protein) emulsified with Freund's complete adjuvant (FCA). Thirty four days later, both fish were re-vaccinated with the same suspension as described above except Freund's incomplete adjuvant was used in place of FCA. Seventeen days after the booster injection, blood was collected from one fish and the anti-serum collected.

Three goldfish weighing between 30-40 g were immunised by IP injection with 0.1 ml of goldfish sera raised against the 50 kDa protein electro-eluted from *A. hydrophila*, and 3 fish were injected with control serum collected from non-vaccinated goldfish. After 24 h all the fish were challenged with 0.1 ml of $2.5 \times 10^7$ ml$^{-1}$. *A. hydrophila* T4 isolate in PBS by IP injection, but on the opposite side to the site where they had been injected with the antiserum (LaFrentz, 2003). Kidney samples from fish which died during the experiment and surviving fish at Day 21 post-challenge were streaked on TSA to confirm specific mortality.

Sequencing and Identification of the 50 kDa Protein of *A. Hydrophila*

A whole cell preparation of *A. hydrophila* T4 isolate in SDS-PAGE sample buffer was prepared for sequencing and analysis of the 50 kDa protein by MALDI-TOF MS. Samples were in-gel reductively alkylated prior to staining with colloidal Coomassie blue, then digested in 0.1% of n-octyl glucoside/20 mM ammonium bicarbonate plus 12.5 µg ml$^{-1}$ trypsin, and the sample (1.5 µl) was spotted from the extract (30 µl) after adding an equal volume of acetonitrile for performing MALDI-TOF MS analysis.

Recombinant 50 kDa Protein Production

Recombinant protein was produced in order to have a sufficient quantity of protein for a large scale vaccination trial. All the recombinant protein work was conducted at the Genomic Laboratory, Tokyo University of Marine Sciences and Technology, Japan.

Polymerase Chain Reaction (PCR) of A. hydrophila 50 kDa Protein Gene

Specific primers were designed to amplify the full length of the 50 kDa protein gene based on the sequence data for the S-layer gene of A. hydrophila published by Thomas and Trust (1995a: see FIG. 8). Restriction sites Nco I and Bgl II were added to the forward and reverse primers respectively to assist its cloning into the expression vector pQE60. The PCR was run for 32 cycles (95° C./5 min; denaturation for 95° C./30 sec; annealing at 55° C./30 sec; elongation at 72° C./1 min and a final elongation step at 72° C./5 min). The primers used were as follows: Forward: acatgggagttaatctggacactggtgc; reverse: gacttgtggtacttgcgtaagtctaga Preparation of PCR Products for Transformation into E. Coli The PCR products were resolved by 1% agarose gel electrophoresis and the DNA was extracted using a DNA purification kit. Digestion of the PCR products and the pQE 60 vector (Qiagen) were carried out overnight at 37° C. Both pQE 60 vectors and PCR products were purified after the digestion process and ligated by mixing 2 µl of vector with 8 µl of PCR products and adding 10 µl ligation high (Cosmo Bio Co Ltd, Tokyo) before incubating it overnight at 16° C.

Transformation of Vectors Carrying 50 kDa Protein Gene into E. Coli

Escherichia coli, M15 (Quiagen, Tokyo, Japan) was transformed with pQE 60 vectors carrying the amplified 50 kDa protein gene of A. hydrophila.

Expression of the Recombinant 50 kDa Protein in E. Coli

The clones containing the 50 kDa protein gene insert identified by PCR, were inoculated into LB broth containing ampicillin (100 µg ml$^{-1}$) and kanamycin (25 µg ml$^{-1}$), and incubated overnight at 37° C. Recombinant protein expression was induced by addition of 1 mM isopropyl-β-thiogalactoside (IPTG) for 4 h. For large scale production, positive clones were cultured in 50 ml of antibiotic supplemented LB broth overnight at 37° C. with vigorous shaking. This culture was transferred to 1 L fresh LB broth and cultured at 37° C. with vigorous shaking. Recombinant protein expression was induced by adding 1 mM IPTG.

Sequencing of the A. Hydrophila T4 Isolate 50 kDa Protein Gene

The whole 50 kDa protein gene of A. hydrophila isolate T4 was sequenced at the Genomic Laboratory, Tokyo University of Marine Sciences and Technology.

Vaccination of Common Carp with Recombinant 50 kDa Protein

Recombinant 50 kDa protein of A. hydrophila diluted in PBS was mixed with montanide adjuvant at a ratio of 30:70 (v/v) to a final antigen concentration of 300 µg ml$^{-1}$. Buffer (PBS) mixed with the adjuvant was also prepared at the same ratio as the antigen to serve as a negative control.

One hundred and fifty common carp (30-40 g) were vaccinated by IP injection with 0.1 ml of the vaccine preparation, and another 150 fish were injected with the PBS adjuvant mixture. All the fish were maintained for 35 days in 1×1 m (Diameter×depth) tanks with recirculating water before challenging with six different isolates of A. hydrophila.

Challenge Studies

Each of the six virulent isolates described above were used to challenge vaccinated fish. Twenty vaccinated and 20 control fish were injected IP with each strain. The concentrations of the bacteria used in the challenge were 1×10$^8$, 2×10$^7$, 2×10$^7$, 5×10$^7$, 7.5×10$^6$ and 2×10$^7$ bacteria ml$^{-1}$ for T4, 98140, 98141, Hh, B2/12 and Vds respectively. All 40 fish within each group were placed in separate glass tank (90 cm length× 47 cm height×40 cm depth) with aeration and recirculating water. The fish were maintained for 16 days post-challenge and dead fish were removed 3 times a day. Samples from the kidney of dead fish and also from surviving fish at the end of the experiment on Day 16 post-challenge were streaked onto TSA.

Statistical Analysis

The results obtained were statically analysed using Chi-square test for survival, comparing the mortality of vaccinated fish with the control group fish after challenging with bacteria.

Results

Antibody Response of Common Carp Infected with Different Isolates of A. hydrophila Antibody Response of Common Carp Infected with A. Hydrophila The antibody levels increased after Day 9 and a positive response was observed on Day 12 post-infection with all the isolates, except for isolate 98141. By Day 21 post-infection, this response had increased for all the isolates, with the highest antibody response recorded against isolate T4 (FIG. 1).

Western Blot Analysis of Common Carp Serum

The WC preparations of A. hydrophila isolates grown in vitro, screened by Western blot with the anti-sera from infected common carp, exhibited a distribution of bands between 20 and 160 kDa (FIG. 2). Carp antibodies bound to antigens ranging from 30-50 kDa for 3 of the virulent isolates, T4, Hh and B2/12. Except for isolate 2D20, one band was observed at approximately 50 kDa.

The antibody response against WC, OMP and ECP preparations of A. hydrophila grown in vitro and in vivo, showed similar profiles among isolates T4, 98141 and Hh (FIG. 3). With all the virulent isolates (T4, Hh, 98141 and Vds), a band was evident at around 50 kDa in WC and OMP preparations. This band was also present in ECP preparations from in vitro cultured bacteria.

The OMP preparations from isolate Vds grown in vitro showed 6 bands between 25 and 50 kDa. A band at 50 kDa was observed in WC and OMP preparations of isolate Catla grown in vitro. A band at around 50 kDa was seen in both WC and OMP preparations from isolate C24li grown in vitro and in vivo. Six bands were seen between 35 and 100 kDa with ECP preparations from bacteria grown in MW cut-off tubes but the bands were weakly stained in the case of bacteria grown in the 100 MW cut off tube.

2D SDS-PAGE Western Blot

The 2D Western blot for A. hydrophila T4 isolate using the antibody raised against the isolate in common carp expressed three spots at approximately 50 kDa with pI values between 5 and 5.7 (FIG. 4).

Figure 6:
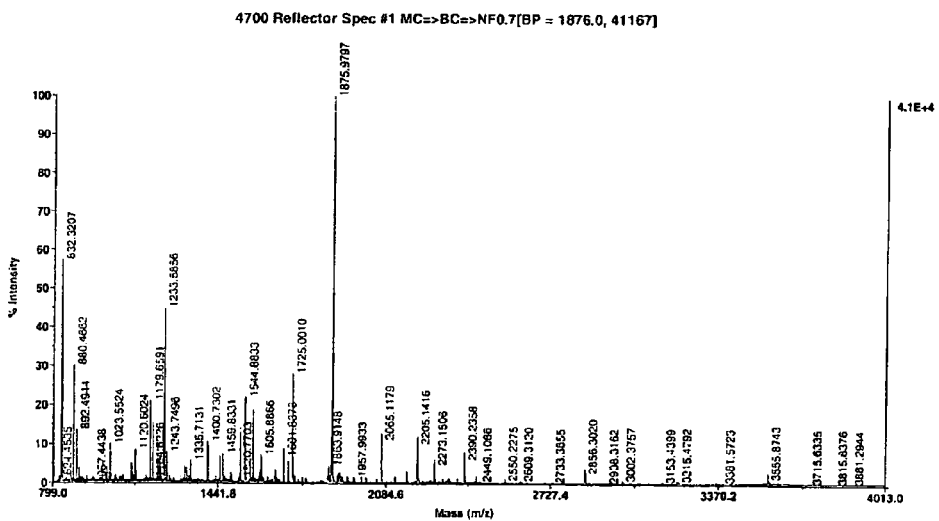

Vaccination and Passive Immunisation of Goldfish with an Electro-Eluted 50 kDa Protein from A. Hydrophila In the vaccination experiment, two control and one vaccinated fish died due to unknown causes before challenging them with A. hydrophila isolate T4. The two fish remaining in the control group died on Day one and Day 4 post-challenge (FIG. 6). One fish from the vaccinated group was also sacrificed one week post-challenge as it was suffering from a severe lesion and A. hydrophila was isolated from swabs taken from the lesion and kidney of the sacrificed fish. The remaining two fish in the vaccinated group were healthy and sacrificed at the end of the experiment, at 21 days post-challenge. All kidney swabs taken from dead fish were positive for *A. hydrophila* while the samples taken from two vaccinated fish at the end of experiment were negative. Though the numbers of fish used in the experiment were low, the RPS value was 66.7%.

The fish serum raised against the 50 kDa protein of *A. hydrophila* used to passively immunise fish, had a titre of 1/16. In the trial, one fish from the control group died two days post-infection and the presence of *A. hydrophila* in its kidney was confirmed using an API 20E strip. No other fish died and no kidneys were positive for the bacteria when remaining fish were sampled at the end of the trial on Day 21.

MALDI-TOF Sequence of the 50 kDa Protein from *A. Hydrophila*

After MALDI-TOF analysis and sequencing, the 50 kDa protein of *A. hydrophila* isolate T4 was identified as a 47.6 kDa S-layer protein (FIG. 7 and FIG. 9). Six bases were found to be different in the whole S-layer genome of *A. hydrophila* T4 isolate (FIG. 9) compared with the S-layer genome sequence of isolate TF7 reported by Thomas and Trust (1995a: FIG. 8). The amino acid sequence shown in FIG. 8 was obtained from the NCBI database.

Production of a Recombinant Protein for the S-Layer of *A. Hydrophila* Isolate T4

Bands at 1353 by on the 1% (w/v) agrose gel verified that the amplification of S-layer genomic DNA was successful (FIG. 10). After transformation of vectors into *E. coli* cells, the presence of the S-layer genome in *E. coli* was confirmed by PCR (FIG. 11*a*) and Western blot (FIG. 11*b*).

Standardisation of the Challenge of Common Carp with *A. Hydrophila*

All six strains T4, 98140, 98141, Hh, B2/12 and Vds were passaged twice through common carp and the bacteria were successfully recovered from both passages. During the first passage, no mortalities occurred in any of the groups of fish, while most fish died upon passaging the bacterium a second time with all strains except T4. The values obtained in the preliminary challenge experiment in which the $LD_{50}$ dose for each strain was determined are given in Table 2.

TABLE 2

The $LD_{50}$ values of *A. hydrophila* strains for common carp

| Strains of *A. hydrophila* | $LD_{50}$ Value (bacteria ml$^{-1}$) |
|---|---|
| T4 | $1 \times 10^8$ |
| Hh | $5 \times 10^7$ |
| 98140 | $2 \times 10^7$ |
| 98141 | $2 \times 10^7$ |
| Vds | $2 \times 10^7$ |
| B2/12 | $7.5 \times 10^6$ |

Vaccination of Common Carp with Recombinant S-Layer Protein of *A. Hydrophila*

In fish challenged with isolate T4, 75% of control and 10% of vaccinated fish died. A high percentage of mortalities were recorded in control fish challenged with isolate T4 compared with fish challenged with the other isolates of *A. hydrophila*. Fifteen percent of the control group died by the first day post-challenge and 25% had died by Day 2 post-challenge. The levels of mortality decreased to 10% by Day 3 post-challenge and thereafter it varied between 5 and 10% until the mortalities stopped by Day 8 post-challenge. The mortality in the vaccinated group was 5% on Day 1 post-challenge and another 5% had died by Day 5 (FIG. 12*a*). A relatively high percentage survival (RPS) value (87%) was found with isolate T4 compared with other isolates (Table 3).

TABLE 3

| Strain of *A. hydrophila* | Total mortality (%) | | Relative percentage survival (%) | P-value (Chi-square test) |
|---|---|---|---|---|
| | Vaccinated fish | Control fish | | |
| T4 | 10 | 75 | 87 | 0.000 |
| Hh | 10 | 65 | 85 | 0.000 |
| 98140 | 10 | 50 | 80 | 0.006 |
| 98141 | 10 | 40 | 75 | 0.028 |
| Vds | 15 | 40 | 62.5 | 0.077 |
| B2/12 | 20 | 45 | 56 | 0.091 |

Mortality of 5% was noted in the control group challenged with isolate Hh on Day 1 post-challenge. However, the mortality increased to 20% by Day 2, 15% occurred on Day 5 and 10% on Day 6. The remainder of mortalities (i.e. 15%) were distributed over the period after Day 7. In the vaccinated group, 5% of mortalities were recorded on the first and third day post-challenge (FIG. 12*b*). The second highest RPS value (85%) in the trial was observed with this isolate.

Fifty-percentage mortality was seen with the control group challenged with isolate 98140. Thirty percent died in the control group during the first two days post-challenge and remainder died over the course of the experiment (16 days post-challenge). Five percent mortality was recorded in the vaccinated group during the first two days post-challenge, and no further mortalities occurred in this group leading to an 80 RPS value for this isolate (FIG. 12*c*).

In the control group challenged with isolate 98141, 25% of mortality occurred over the first two days of the experiment and thereafter 15% mortalities occurred. The mortality with the vaccinated group was similar to that of the mortality recorded with vaccinated group challenged with isolate 98140 (FIG. 12*d*). An RPS value of 75% was recorded with this isolate.

The control group challenged with isolate Vds experienced a 10% mortality on Day 1, Day 2 and Day 5 post-challenge, while 5% mortalities occurred on the third and sixth day post-challenge (FIG. 12*e*). A total of 15% mortality occurred in the vaccinated group distributed over Day 2, 3 and 5 post-challenge. The RPS value with this isolate was 62.5%.

Percentage mortality in the control group rose to 30% during the first two days after challenging the fish with isolate B2/12. Another 15% mortality occurred in this group over the remainder of the experiment. The highest percentage mortality amongst vaccinated fish was recorded in the group challenged with B2/12. Ten percent mortality was observed in this group on the next day post-challenge and 5% of mortality occurred on the second day and the third day post-challenge (FIG. 12*f*). The RPS value was low (56%) with this isolate compared to other isolates.

All the fish that died during the experiment showed the presence of *A. hydrophila* in their kidneys. In contrast, *A. hydrophila* was not cultured from kidney swabs taken from the surviving fish except very few colonies from one fish in the vaccinated group challenged with isolate 98140 and one fish in the control group challenged with isolate 98141. Statistical analysis revealed that survival against isolates T4, 98140, 98141 and Hh were significant in vaccinated fish compared to control fish, while levels of survival were not statistically significant for isolates B2/12 and Vds (Table 3).

Discussion

In this study, common carp were infected with *A. hydrophila* and the anti-sera produced were used to identify immunogenic components of the bacterium. The different *A. hydrophila* isolates examined elicited a variety of responses in common carp, as determined by ELISA. An increase in antibody response against *A. hydrophila* was seen after Day 9 post-infection for all the isolates except one (98141). Antibody response peaked on Day 12 post-infection for two isolates (Hh and Catla) and on Day 21 post-infection for three isolates (T4, Vds and C24li). The antibody response of common carp did not show any differentiation between virulent and avirulent isolates of *A. hydrophila*. This may be due to differences in the ability of the immune system of the host to respond to foreign agents.

Western blot analysis using the anti-sera produced on Day 21 post-infection, against different strains of *A. hydrophila*, showed differences in the profiles between the isolates. However, when pooled sera (from common carp infected with 6 different isolates) were used to examine the response against the 14 isolates of *A. hydrophila* (described in Table 1), a band at around 50 kDa was observed in all the isolates grown in vitro, except for isolate 2D20. Moreover, bands from 30-50 kDa were stained in the profiles of 3 of the virulent isolates, T4, Hh and B2/12 grown in vitro. A band at around 50 kDa was seen with all the preparations (WC, OMP, ECP) from the virulent isolates grown both in vitro and in vivo compared with avirulent isolates, with the exception of the ECP from bacteria grown in vivo.

The 2D Western blot analysis of *A. hydrophila* (T4 isolate) WC revealed 3 spots at approximately 50 kDa between 5 and 5.7 pI range when serum raised against T4 isolates was used. The results of the 1D and 2D Western blot analysis suggest that a molecule at approximately 50 kDa (ranging between 47 and 51 kDa) might be one of the major immunogenic components of *A. hydrophila*.

The 50 kDa protein of *A. hydrophila* was considered to be the most immunogenic and most homogenous protein, recognised on each of the *A. hydrophila* isolates examined. The 50 kDa protein conferred protection in goldfish against *A. hydrophila* in the direct immunisation trial.

After MALDI-TOF MS sequenceing, six bases were found to be different in the whole S-layer genome of *A. hydrophila* T4 isolate (FIG. 9) compared with the S-layer genome sequence of isolate TF7 reported by Thomas and Trust (1995a: FIG. 8). This in turn could result with changes in 4 amino acids in the S-layer protein of *A. hydrophila* isolate T4 compared with S-layer amino acid sequence reported for isolate TF7.

A recombinant S-layer protein of *A. hydrophila* was produced to confirm the protection efficacy of this protein in common carp against different isolates of *A. hydrophila*. The recombinant S-layer protein proved reactive in Western blot analysis against anti-*A. hydrophila* T4 common carp serum and it was used to vaccinate a number of fish. These fish were then challenged with a range of different *A. hydrophila* isolates. High mortality rate was observed both in the vaccinated and control group within two days post-challenge compared with the mortality from Day 3 post-challenge as described in FIG. 4.8. The protection elicited by the S-layer protein in vaccinated fish indicates a potential role for this protein in the virulence of *A. hydrophila*.

The S-layer protein antigen of *A. hydrophila* appears to have conferred protection against the different isolates of *A. hydrophila* tested, although the RPS values of carp did vary between the different challenge isolates.

No mortalities occurred in any of the groups of fish after Day 11 post-challenge in the vaccination trial described in this Chapter. Moreover, no colonies of *A. hydrophila* grew from the kidney swabs taken from surviving fish at the end of experiment except for two fish. This suggests that most of the surviving fish in the control group had cleared the bacterium through their own immune response, as fish can produce an antibody response against different components of bacterium and clear the bacteria in blood circulatory system within seven days post-infection (Leung and Stevenson, 1988b; Chandran et al., 2002b).

REFERENCES

Asha A., Nayak D. K., Shankar K. M. and Mohan C. V. (2004) Antigen expression in biofilm cells of *Aeromonas hydrophila* employed in.oral vaccination of fish. *Fish & Shellfish Immunology* 16, 429-436.

Azad I. S., Shankar K. M., Mohan C. V. and Kalita B. (1999) Biofilm vaccine of *Aeromonas hydrophila*—standardization of dose and duration for oral vaccination of carps. *Fish & Shellfish Immunology* 9, 519-528.

Azad I. S., Shankar K. M., Mohan C. V. and Kalita B. (2000a) Uptake and processing of biofilm and free-cell vaccines of *Aeromonas hydrophila* in Indian major carps and common carp following oral vaccination—antigen localization by a monoclonal antibody. *Diseases of Aquatic Organisms* 43, 103-108.

Baba T., Imamura J., Izawa K. and Ikeda K. (1988a) Cell-mediated protection in carp, *Cyprinus carpio* L., against *Aeromonas hydrophila*. *Journal of Fish Diseases* 11, 171-178.

Baba T., Imamura J., Izawa K. and Ikeda K. (1988b) Immune protection in carp, *Cyprinus carpio* L., after immunization with *Aeromonas hydrophila* crude lipopolysaccharide. *Journal of Fish Diseases* 11, 237-244.

Chandran M. R., Aruna B. V., Logambal S. M. and Dinakaran M. R. (2002b) Immunisation of Indian major carps against *Aeromonas hydrophila* by intraperitoneal injection. *Fish & Shellfish Immunology* 13, 1-9.

Chandran M. R., Aruna B. V., Logambal S. M. and Michael R. D. (2002a) Field immunization of Indian major carps against *Aeromonas hydrophila* by Dooley J. S. G., Lallier R. and Trust T. J. (1986) Surface antigens of virulent strains of *Aeromonas hydrophila*. *Veterinary Immunology and Immunopathology* 12, 339-344.

Ellis A. E. (1988) General principles of fish vaccination. In: Fish Vaccination (Ed. by Ellis A. E.), Academic Press, London, pp. 2031.

Esteve C., Amaro C., Garay E., Santos Y. and Toranzo A. E. (1995) Pathogenicity of live bacteria and extracellular products of motile *Aeromonas* isolated from eels. *Journal of Applied Bacteriology* 78, 555-562.

Fang H. M., Ge R. and Sin Y. M. (2004) Cloning, characterisation and expression of *Aeromonas hydrophila* major adhesin. *Fish & Shellfish Immunology* 16, 645-658.

Janda J. M., Guthertz L. S., Kokka R. P. and Shimada T. (1994b) *Aeromonas* species in septicemia: Laboratory characteristics and clinical observations. *Clinical Infectious Diseases* 19, 77-83.

Khashe S., Hill W. and Janda J. M. (1996) Characterization of *Aeromonas hydrophila* strains of clinical, animal, and environmental origin expressing the O:34 antigen. *Current Microbiology* 33, 104-108.

Kusuda R., Chen C. and Kawai K. (1987) Changes in the agglutinating antibody titre and serum protein composition of colored carp after immunization with *Aeromonas hydrophila*. *Fish Pathology* 22, 141-146.

LaFrentz B. R., LaPatra S. E., Jones G. R. and Cain K. D. (2003) Passive immunisation of rainbow trout, *Oncorhynchus mykiss* (Walbaum), aganist *Flavobacterium psychrophilum*, the causative agent of bacterial coldwater disease and rainbow trout fry syndrome. *Journal of Fish Diseases* 26, 377-384.

Lamers C. H. J., De Haas M. J. H. and Van Muiswinkel W. B. (1985) The reaction of the immune system of fish to vaccination: Development of immunological memory in carp, *Cyprinus carpio* L., following direct immersion in *Aeromonas hydrophila* bacterin. *Journal of Fish Diseases* 8, 253-262.

Leung K. Y. and Stevenson R. M. W. (1988b) Tn5-induced protease-deficient strains of *Aeromonas hydrophila* with reduced virulence for fish. *Infection and Immunity* 56, 2639-2644.

Leung K. Y., Wong L. S., Low K. W. and Sin Y. M. (1997) Mini-Tn5 induced growth- and protease-deficient mutants of *Aeromonas hydrophila* as live vaccines for blue gourami, *Trichogaster trichopterus* (Pallas). *Aquaculture* 158, 11-22.

Leung K. Y., Yeap I. V., Lam T. J. and Sin Y. M. (1995) Serum resistance as a good indicator for virulence in *Aeromonas hydrophila* strains isolated from diseased fish in South-East Asia. *Journal of Fish Diseases* 18, 511-518.

Loghothetis P. N. and Austin B. (1994) Immune response of rainbow trout (*Oncorhynchus mykiss*, Walbaum) to *Aeromonas hydrophila*. *Fish & Shellfish Immunology* 4, 239-254.

Loghothetis P. N. and Austin B. (1996b) Antibody responses of rainbow trout (*Oncorhynchus mykiss*, Walbaum) to live *Aeromonas hydrophila* as assessed by various antigen preparations. *Fish & Shellfish Immunology* 6, 455-464.

Majumdar T., Ghosh D., Datta S., Sahoo C., Pal J. and Mazumder S. (2006) An attenuated plasmid-cured strain of *Aeromonas hydrophila* elicits protective immunity in *Clarias batrachus* L. *Fish & Shellfish Immunology* in press.

Moral C. H., Del Castillo E. F., Fierro P. L., Cortes A. V., Castillo J. A., Soriano A. C., Salazar M. S., Peralta B. R. and Carrasco G. N. (1998) Molecular characterization of the *Aeromonas hydrophila* aroA gene and potential use of an auxotrophic aroA mutant as a live attenuated vaccine. *Infection and Immunity* 66, 1813-1821.

Munn C. B. (1994) The use of recombinant DNA technology in the development of fish vaccines. *Fish & Shellfish Immunology* 4, 459-473.

Nayak D. K., Asha A., Shankar K. M. and Mohan C. V. (2004b) Evaluation of biofilm of *Aeromonas hydrophila* for oral vaccination of *Clarias batrachus*—a carnivore model. *Fish & Shellfish Immunology* 16, 613-619.

Newman S. G. (1993) Bacterial vaccines for fish. *Annual Review of Fish Diseases* 3, 145-185.

Olivier, G., Lallier, R. and Lariviere, S. (1981) A toxigenic profile of *Aeromonas hydrophila* and *Aeromonas sobria* isolated from fish. *Canadian Journal of Microbiology* 27, 330-333.

Rahman M. H. and Kawai K. (2000) Outer membrane proteins of *Aeromonas hydrophila* induce protective immunity in goldfish. *Fish & Shellfish Immunology* 10, 379-382.

Sakazaki R. and Shimada T. (1984) O-serogrouping scheme for mesophilic *Aeromonas* strains. *Japanese Journal of Medical Science and Biology* 37, 247-255.

Shotts E. B., Gaines J. L., Martin L. and Prestwood A. K. (1972) *Aeromonas*-induced deaths among fish and reptiles in an eutrophic inlands lake. *Journal of the American Veterinary Medical Association* 161, 603-607.

Stevenson R. M. W. (1988) Vaccination against *Aeromonas hydrophila*. In: Fish vaccination (Ed. by Ellis A. E.), Academic press, New York, pp. 112-123.

Thomas S. R. and Trust T. J. (1995a) Tyrosine phosphorylation of the tetragonal paracrystalline array of *Aeromonas hydrophila:* Molecular cloning and high-level expression of the S-layer protein gene. *Journal of Molecular Biology* 245, 568-581.

Vivas J., Riano J., Carracedo B., Razquin B. E., Lopez-Fierro P., Naharro G. and Villena A. J. (2004b) The auxotrophic aroA mutant of *Aeromonas hydrophila* as a live attenuated vaccine against *A. salmonicida* infections in rainbow trout (*Oncorhynchus mykiss*). *Fish & Shellfish Immunology* 16, 193-206.

Vivas J., Carracedo B., Riano J., Razquin B. E., Lopez-Fierro P., Acosta F., Naharro G. and Villena A. J. (2004c) Behavior of an *Aeromonas hydrophila* aroA live vaccine in water microcosms. *Applied and Environmental Microbiology* 70, 2702-2708.

Vivas J., Razquin B., Lopez-Fierro P. and Villena A. J. (2005) Modulation of the immune response to an *Aeromonas hydrophila* aroA live vaccine in rainbow trout: effect of culture media on the humoral immune response and complement consumption. *Fish & Shellfish Immunology* 18, 223-233.

The invention claimed is:

1. An isolated protein from the S-layer of *A. hydrophila* comprising the amino acid sequence of SEQ ID NO:4 for use in raising an immune response in an organism.

2. An immunogenic formulation for use in raising an immune response in an organism, comprising an isolated protein comprising the amino acid sequence of SEQ ID NO:4, representing an immunogenic S-layer protein from *A. hydrophila*.

3. A fusion protein comprising a carrier polypeptide and the isolated protein according to claim 1.

4. A method for immunising freshwater fish or shellfish against *A. hydrophila* by administering to the fish/shellfish a fusion protein according to claim 3.

5. A method for immunising freshwater fish or shellfish against *A. hydrophila* by administering to the fish/shellfish a composition comprising the isolated protein according to claim 1.

6. A composition comprising the isolated protein according to claim 1 and an adjuvant.

7. The formulation according to claim 2 further comprising an adjuvant.

8. The formulation according to claim 2 further comprising a carrier.

9. The method of claim 5, wherein the composition is administered by direct injection.

10. The method of claim 9, wherein the composition is administered by intraperitoneal or intramuscular injection.

11. A method for immunising freshwater fish or shellfish against *A. hydrophila*, comprising exposing the fish or shellfish to a composition comprising the isolated protein of claim 1.

12. The method of claim 11, wherein the fish or shellfish is exposed to the isolated protein by bath immersion, ingestion, topical administration, or combinations thereof.

13. A method for immunising freshwater fish or shellfish against *A. hydrophila*, comprising exposing the fish or shellfish to a composition comprising the fusion protein of claim 3.

14. The method of claim 13, wherein the fish or shellfish is exposed to the fusion protein by bath immersion, ingestion, topical administration, or combinations thereof.

15. The method of claim 4, wherein the fusion protein is administered by direct injection.

16. The method of claim 15, wherein the fusion protein is administered by intraperitoneal or intramuscular injection.

17. An isolated protein from the S-layer of *A. hydrophila* comprising the amino acid sequence of SEQ ID NO:4, representing an immunogenic S-layer protein from *A. hydrophila*.

* * * * *

SEQUENCE LISTING

<160> NUMBER OF SEQ ID NOS: 4

<210> SEQ ID NO 1
<211> LENGTH: 1419
<212> TYPE: DNA
<213> ORGANISM: Aeromonas hydrophila

<400> SEQUENCE: 1

```
atgattctaa tgaaaaagac actgattgca ctggccgttg ctggtctgag ctttaacgct      60
gctgcagtta atctggacac tggtgctggc gtttctaagt ttgctagcga aatcaaagtt     120
gatggcgcgg caggtactac cttgggtacc gcagccggtg ctgctatgaa tgcagtgagc     180
aagctgggtt tctctatttc taccggtaac aagcgttaca ttcgttacga tgtaactggt     240
ggttcactgg ctggtgtcgc tgttgcggac ttgaccttgg ttggtggtac tcctgttgct     300
gtagttgcag ctgatagctc ctttgttatc tctcagaccg ccgctgatgg tagctttgtg     360
```

-continued

```
atcgttgaag ttgttgctaa gaaagacatc cctgctgatg cagtgatgac ctccaaagcc    420
gatggtcgtg tgaacgttaa gacaaaaaat ggcgtagcta tcagctatcg cctgttcgag    480
actgctctgg atgccgttgc taacgatcca gctaagaccc tggccaaggc aaatggtcaa    540
ctgctgactt tctccccagc tatcctcgcc aaagttgaga agaagggttc tgccgacaag    600
atcgacgtga ccgagtcttc catgaagttt gttaccaatg cgaatgttaa agctactgat    660
accatcctgg gtcaagtaag catcactgca gacgtaaaca ctcttttggc taacggtact    720
cccgtggctg ctaccagtga tattctgaat gcaagcaaac tggttgttaa tggtgatttc    780
tctgcaggtg cagtagacgc cgataacaaa ctggttctgg gtaccgtcaa gctgaatgct    840
gccaatgcta ctaaagttga agccgcgaaa gctgagctgg ctgtggcaga tgcaggtatt    900
ggtgcagcag ctccagcagg taacatcagc tactttgttg gtggcaaagc tcctatcgct    960
ccgcaggctg taactgctac tttcgttccg gttgtaaaag ctggttatga gttggctgat   1020
gtaaatctgg gcgaaattgg tgtgctgaac aaaaatggtt ccaccaaaga agctaacctg   1080
gtgctggctc cagataccct cttacaccaa ctggtgcgta tctccaacac ctccaacatc   1140
gctggtaagt tctttgtgac tgcttatgct gatgatggta agtctgtaag cttcgcactg   1200
tctgatgttg ctggtcagcc ggctgttctg gaagctggcg cctccaccaa gcagatgaaa   1260
gtggctgata tctatgctgc tgcccaagcc aaaggtctgg ctctgactgg tgacaagaaa   1320
ctgcgtctga agttgaaggt gaagtggct tccctgagcc tgcagaacta caccgtctcc   1380
aaagacggta acgctctgaa caccatgaac gcattctaa                          1419
```

<210> SEQ ID NO 2
<211> LENGTH: 472
<212> TYPE: PRT
<213> ORGANISM: Aeromonas hydrophila

<400> SEQUENCE: 2

```
Met Ile Leu Met Lys Lys Thr Leu Ile Ala Leu Ala Val Ala Gly Leu
1               5                  10                  15

Ser Phe Asn Ala Ala Ala Val Asn Leu Asp Thr Gly Ala Gly Val Ser
            20                  25                  30

Lys Phe Ala Ser Glu Ile Lys Val Asp Gly Ala Ala Gly Thr Thr Leu
        35                  40                  45

Gly Thr Ala Ala Gly Ala Ala Met Asn Ala Val Ser Lys Leu Gly Phe
    50                  55                  60

Ser Ile Ser Thr Gly Asn Lys Arg Tyr Ile Arg Tyr Asp Val Thr Gly
65                  70                  75                  80

Gly Ser Leu Ala Gly Val Ala Val Ala Asp Leu Thr Leu Val Gly Gly
                85                  90                  95

Thr Pro Val Ala Val Val Ala Ala Asp Ser Ser Phe Val Ile Ser Gln
            100                 105                 110

Thr Ala Ala Asp Gly Ser Phe Val Ile Val Glu Val Val Ala Lys Lys
        115                 120                 125

Asp Ile Pro Ala Asp Ala Val Met Thr Ser Lys Ala Asp Gly Arg Val
130                 135                 140

Asn Val Lys Thr Lys Asn Gly Val Ala Ile Ser Tyr Arg Leu Phe Glu
145                 150                 155                 160

Thr Ala Leu Asp Ala Val Ala Asn Asp Pro Ala Lys Thr Leu Ala Lys
                165                 170                 175

Ala Asn Gly Gln Leu Leu Thr Phe Ser Pro Ala Ile Leu Ala Lys Val
            180                 185                 190
```

-continued

```
Glu Lys Lys Gly Ser Ala Asp Lys Ile Asp Val Thr Glu Ser Ser Met
    195                 200                 205
Lys Phe Val Thr Asn Ala Asn Val Lys Ala Thr Asp Thr Ile Leu Gly
    210                 215                 220
Gln Val Ser Ile Thr Ala Asp Val Asn Thr Leu Leu Ala Asn Gly Thr
225                 230                 235                 240
Pro Val Ala Ala Thr Ser Asp Ile Leu Asn Ala Ser Lys Leu Val Val
                245                 250                 255
Asn Gly Asp Phe Ser Ala Gly Ala Val Asp Ala Asp Asn Lys Leu Val
                260                 265                 270
Leu Gly Thr Val Lys Leu Asn Ala Ala Asn Ala Thr Lys Val Glu Ala
            275                 280                 285
Ala Lys Ala Glu Leu Ala Val Ala Asp Ala Gly Ile Gly Ala Ala Ala
        290                 295                 300
Pro Ala Gly Asn Ile Ser Tyr Phe Val Gly Gly Lys Ala Pro Ile Ala
305                 310                 315                 320
Pro Gln Ala Val Thr Ala Thr Phe Val Pro Val Lys Ala Gly Tyr
                325                 330                 335
Glu Leu Ala Asp Val Asn Leu Gly Glu Ile Gly Val Leu Asn Lys Asn
                340                 345                 350
Gly Ser Thr Lys Glu Ala Asn Leu Val Leu Ala Pro Asp Thr Ser Tyr
            355                 360                 365
Thr Asn Leu Val Arg Ile Ser Asn Thr Ser Asn Ile Ala Gly Lys Phe
        370                 375                 380
Phe Val Thr Ala Tyr Ala Asp Asp Gly Lys Ser Val Ser Phe Ala Leu
385                 390                 395                 400
Ser Asp Val Ala Gly Gln Pro Ala Val Leu Glu Ala Gly Ala Ser Thr
                405                 410                 415
Lys Gln Met Lys Val Ala Asp Ile Tyr Ala Ala Gln Ala Lys Gly
                420                 425                 430
Leu Ala Leu Thr Gly Asp Lys Lys Leu Arg Leu Lys Val Glu Gly Glu
        435                 440                 445
Val Ala Ser Leu Ser Leu Gln Asn Tyr Thr Val Ser Lys Asp Gly Asn
    450                 455                 460
Ala Leu Asn Thr Met Asn Ala Phe
465                 470

<210> SEQ ID NO 3
<211> LENGTH: 1419
<212> TYPE: DNA
<213> ORGANISM: Aeromonas hydrophila

<400> SEQUENCE: 3
atgattctaa tgaaaaagac actgattgca ctggccgttg ctggtctgag ctttaacgct    60
gctgcagtta atctggacac tggtgctggt gtttctaagt ttgctagcga aatcaaagtt   120
gatggcgcgg caggtactac cttgggtacc gcagccggtg ctgctatgaa tgcagtgagc   180
aagctgggtt tctctatttc taccggtaac aagcgttaca ttcgttacga tgtaactggt   240
ggttcactgg ctggtgtcgc tgttgcggac ttgaccttgg ttggtggtac tcctgttgct   300
gtagttgcag ctgatagctc ctttgttatc tctcagaccg ccgctgatgg tagctttgtg   360
atcgttgaag ttgttgctaa gaaagacatc cctgctgatg cagtgatgac ctccaaagcc   420
gatggtcgtg tgaacgttaa gacaaaaat ggcgtagcta tcagctatcg cctgttcgag   480
actgctctgg atgccgttgc taacgatcca gctaagaccc tggccaaggc aaatggtcaa   540
```

```
ctgctgactt tctccccagc tatcctcgcc aaagttgaga agaagggttc tgccgacaag     600
atcgacgtga ccgagtcttc catgaagttt gttaccaatg cgaatgttaa agctactgat     660
accatcctgg gtcaagtaag catcactgca gacgtaaaca ctcttttggc taacggtact     720
cccgtggctg ctaccagtga tattctgaat gcaagcaaac tggttgttaa tggtgatttc     780
tctgcaggtg cagtagacgc cgataacaaa ctggttctgg gtaccgtcaa gctgaatgct     840
gccaatgcta ctaaagttga agccgcgaaa gctgagctgg ctgtggcaga tgcaggtatt     900
ggtgcagcag ctccagcagg taacatcagc tactttgttg gtggcaaagc tcctatcgct     960
ccgcagtctg taactgctac tttcgttccg gttgtaaaag ctggttatga gttggctgat    1020
gtaaatctgg gcgaaattgg tgtgctgaac aaaaatggtt ccaccaaaga agctaacctg    1080
gtgctggctc cagataccct cttacaccaa ctggtgcgta tctccaacac ctccaacatc    1140
gctggtaagt tctttgtgac tgcttatgct gatgatggta agtctgtaag cttcgcactg    1200
tctgatgttg ctggtcagcc ggctgttctg gacgctggcg cctccaccac gcagatgaaa    1260
gtggctgata tctatgctgc tgcccaagcc aaaggtctgg ctctgactgg tgacaagaaa    1320
ctgcgtctga agttgaagg tgaagtggct tccctgagcc tgcagaacta caccgtctcc    1380
aaagacggta acgctctgaa caccatgaac gcattctaa                          1419

<210> SEQ ID NO 4
<211> LENGTH: 472
<212> TYPE: PRT
<213> ORGANISM: Aeromonas hydrophila

<400> SEQUENCE: 4

Met Ile Leu Met Lys Lys Thr Leu Ile Ala Leu Ala Val Ala Gly Leu
1               5                   10                  15

Ser Phe Asn Ala Ala Val Asn Leu Asp Thr Gly Ala Gly Val Ser
            20                  25                  30

Lys Phe Ala Ser Glu Ile Lys Val Asp Gly Ala Ala Gly Thr Thr Leu
        35                  40                  45

Gly Thr Ala Ala Gly Ala Ala Met Asn Ala Val Ser Lys Leu Gly Phe
    50                  55                  60

Ser Ile Ser Thr Gly Asn Lys Arg Tyr Ile Arg Tyr Asp Val Thr Gly
65                  70                  75                  80

Gly Ser Leu Ala Gly Val Ala Val Ala Asp Leu Thr Leu Val Gly Gly
                85                  90                  95

Thr Pro Val Ala Val Ala Ala Asp Ser Ser Phe Val Ile Ser Gln
            100                 105                 110

Thr Ala Ala Asp Gly Ser Phe Val Ile Val Glu Val Val Ala Lys Lys
        115                 120                 125

Asp Ile Pro Ala Asp Ala Val Met Thr Ser Lys Ala Asp Gly Arg Val
    130                 135                 140

Asn Val Lys Asn Lys Asn Gly Val Ala Ile Ser Tyr Arg Leu Phe Glu
145                 150                 155                 160

Thr Ala Leu Asp Ala Val Ala Asn Asp Pro Ala Lys Thr Leu Ala Lys
                165                 170                 175

Ala Asn Gly Gln Leu Leu Thr Phe Ser Pro Ile Leu Ala Lys Val
            180                 185                 190

Glu Lys Lys Gly Ser Ala Asp Lys Ile Asp Val Thr Glu Ser Ser Met
        195                 200                 205

Lys Phe Val Thr Asn Ala Asn Val Lys Ala Thr Asp Thr Ile Leu Gly
    210                 215                 220
```

-continued

```
Gln Val Ser Ile Thr Ala Asp Val Asn Thr Leu Leu Ala Asn Gly Thr
225                 230                 235                 240

Pro Val Ala Ala Thr Ser Asp Ile Leu Asn Ala Ser Lys Leu Val Val
                245                 250                 255

Asn Gly Asp Phe Ser Ala Gly Ala Val Asp Ala Asp Asn Lys Leu Val
            260                 265                 270

Leu Gly Thr Val Lys Leu Asn Ala Ala Asn Ala Thr Lys Val Glu Ala
        275                 280                 285

Ala Lys Ala Glu Leu Ala Val Ala Asp Ala Gly Ile Gly Ala Ala Ala
    290                 295                 300

Pro Ala Gly Asn Ile Ser Tyr Phe Val Gly Gly Lys Ala Pro Ile Ala
305                 310                 315                 320

Pro Gln Ser Val Thr Ala Thr Phe Val Pro Val Val Lys Ala Gly Tyr
                325                 330                 335

Glu Leu Ala Asp Val Asn Leu Gly Glu Ile Gly Val Leu Asn Lys Asn
            340                 345                 350

Gly Ser Thr Lys Glu Ala Asn Leu Val Leu Ala Pro Asp Thr Ser Tyr
        355                 360                 365

Thr Asn Leu Val Arg Ile Ser Asn Thr Ser Asn Ile Ala Gly Lys Phe
    370                 375                 380

Phe Val Thr Ala Tyr Ala Asp Asp Gly Lys Ser Val Ser Phe Ala Leu
385                 390                 395                 400

Ser Asp Val Ala Gly Gln Pro Ala Val Leu Asp Ala Gly Ala Ser Thr
                405                 410                 415

Thr Gln Met Lys Val Ala Asp Ile Tyr Ala Ala Ala Gln Ala Lys Gly
            420                 425                 430

Leu Ala Leu Thr Gly Asp Lys Lys Leu Arg Leu Lys Val Glu Gly Glu
        435                 440                 445

Val Ala Ser Leu Ser Leu Gln Asn Tyr Thr Val Ser Lys Asp Gly Asn
    450                 455                 460

Ala Leu Asn Thr Met Asn Ala Phe
465                 470
```